(12) United States Patent
Hackett et al.

(10) Patent No.: US 7,919,583 B2
(45) Date of Patent: Apr. 5, 2011

(54) INTEGRATION-SITE DIRECTED VECTOR SYSTEMS

(75) Inventors: Perry B. Hackett, Shoreview, MN (US); Jeffrey Essner, Minneapolis, MN (US)

(73) Assignee: Discovery Genomics, Inc., Minneapolis, MN (US)

( * ) Notice: Subject to any disclaimer, the term of this patent is extended or adjusted under 35 U.S.C. 154(b) by 256 days.

(21) Appl. No.: 11/198,987

(22) Filed: Aug. 8, 2005

(65) Prior Publication Data

US 2007/0031380 A1 Feb. 8, 2007

(51) Int. Cl.
*C07K 14/00* (2006.01)
*C12N 15/11* (2006.01)
*C12N 15/62* (2006.01)
*C07H 21/04* (2006.01)

(52) U.S. Cl. ............... 530/350; 435/320.1; 536/23.4

(58) Field of Classification Search .................. None
See application file for complete search history.

(56) References Cited

U.S. PATENT DOCUMENTS

| | | | |
|---|---|---|---|
| 5,110,802 A | 5/1992 | Cantin et al. | |
| 5,144,019 A | 9/1992 | Rossi et al. | |
| 5,149,796 A | 9/1992 | Rossi et al. | |
| 5,272,262 A | 12/1993 | Rossi et al. | |
| 5,626,877 A | 5/1997 | Amsden et al. | |
| 5,750,380 A | 5/1998 | Itakura et al. | |
| 5,891,108 A | 4/1999 | Leone et al. | |
| 5,972,027 A | 10/1999 | Johnson | |
| 5,985,575 A | 11/1999 | Wickens et al. | |
| 5,985,661 A | 11/1999 | Rossi | |
| 6,013,516 A | 1/2000 | Verma et al. | |
| 6,041,252 A | 3/2000 | Walker et al. | |
| 6,057,104 A | 5/2000 | Hasty | |
| 6,071,305 A | 6/2000 | Brown et al. | |
| 6,074,673 A | 6/2000 | Guillen | |
| 6,083,996 A | 7/2000 | Büyüktimkin et al. | |
| 6,086,582 A | 7/2000 | Altman et al. | |
| 6,086,912 A | 7/2000 | Gilman | |
| 6,110,498 A | 8/2000 | Rudnic et al. | |
| 6,126,919 A | 10/2000 | Stefely et al. | |
| 6,132,765 A | 10/2000 | DiCosmo et al. | |
| 6,136,295 A | 10/2000 | Edwards et al. | |
| 6,142,939 A | 11/2000 | Eppstein et al. | |
| 6,235,312 B1 | 5/2001 | Hobbs et al. | |
| 6,235,313 B1 | 5/2001 | Mathiowitz et al. | |
| 6,245,349 B1 | 6/2001 | Yiv et al. | |
| 6,251,079 B1 | 6/2001 | Gambale et al. | |
| 6,283,947 B1 | 9/2001 | Mirzaee | |
| 6,283,949 B1 | 9/2001 | Roorda | |
| 6,287,792 B1 | 9/2001 | Pardridge et al. | |
| 6,296,621 B1 | 10/2001 | Masuda et al. | |
| 6,296,832 B1 | 10/2001 | Ruoslahti et al. | |
| 6,309,370 B1 | 10/2001 | Haim et al. | |
| 6,309,375 B1 | 10/2001 | Glines et al. | |
| 6,309,380 B1 | 10/2001 | Larson et al. | |
| 6,309,410 B1 | 10/2001 | Kuzma et al. | |
| 6,317,629 B1 | 11/2001 | Haak et al. | |
| 6,346,272 B1 | 2/2002 | Viegas et al. | |
| 6,350,780 B1 | 2/2002 | Garst et al. | |
| 6,379,382 B1 | 4/2002 | Yang | |
| 6,387,124 B1 | 5/2002 | Buscemi et al. | |
| 6,387,397 B1 | 5/2002 | Chen et al. | |
| 6,410,017 B1 | 6/2002 | Weisgerber et al. | |
| 6,479,626 B1 * | 11/2002 | Kim et al. ................. 530/300 |
| 6,489,458 B2 | 12/2002 | Hackett et al. | |
| 6,555,692 B1 | 4/2003 | Dervan | |
| 6,562,570 B1 | 5/2003 | Rossi et al. | |
| 6,576,759 B2 | 6/2003 | Zeng et al. | |
| 6,720,478 B1 | 4/2004 | Mahajan et al. | |
| 6,794,136 B1 | 9/2004 | Eisenberg et al. | |
| 6,809,183 B2 | 10/2004 | Mahajan | |
| 6,903,185 B2 | 6/2005 | Kim et al. | |
| 2003/0036056 A1 | 2/2003 | Rossi et al. | |
| 2003/0119017 A1 | 6/2003 | McSwiggen | |
| 2003/0124513 A1 | 7/2003 | McSwiggen | |
| 2003/0125281 A1 | 7/2003 | Lewis et al. | |
| 2003/0130186 A1 | 7/2003 | Vargeese et al. | |
| 2003/0139363 A1 | 7/2003 | Kay et al. | |
| 2003/0144239 A1 | 7/2003 | Agami et al. | |
| 2003/0148519 A1 | 8/2003 | Engelke et al. | |
| 2003/0153519 A1 | 8/2003 | Kay et al. | |
| 2003/0157691 A1 | 8/2003 | Qin et al. | |
| 2003/0166282 A1 | 9/2003 | Brown et al. | |
| 2003/0166512 A1 | 9/2003 | Xie | |

(Continued)

FOREIGN PATENT DOCUMENTS

WO    WO 92/06988    4/1992

(Continued)

OTHER PUBLICATIONS

Biet et al (Stimulation of RecA-Mediated D-loop Formation by Oligonucleotide-Directed Triple-Helix Formation: Guided Homologous Recombination (GOREC). Biochemistry, 2001. 40:1779-1786.*

(Continued)

*Primary Examiner* — Michael Burkhart
(74) *Attorney, Agent, or Firm* — Dardi & Herbert, PLLC

(57) ABSTRACT

Some aspects of the application describe materials and methods for making a molecular tether. A molecular tether, in certain embodiments, includes a target-DNA-binding domain having a specific binding affinity for a target-DNA segment in a host chromosome, a carrier-binding domain that specifically binds to a DNA segment on a carrier, and a spacer covalently bonded to the target DNA-binding domain and the carrier-binding domain.

22 Claims, 4 Drawing Sheets

U.S. PATENT DOCUMENTS

| | | | |
|---|---|---|---|
| 2003/0217376 A1* | 11/2003 | Ebens et al. | 800/8 |
| 2004/0077572 A1 | 4/2004 | Hackett et al. | |
| 2004/0203158 A1 | 10/2004 | Hackett et al. | |
| 2004/0224336 A1 | 11/2004 | Wagner | |
| 2005/0037385 A1 | 2/2005 | Choo et al. | |
| 2005/0112620 A1* | 5/2005 | Chan | 435/6 |

FOREIGN PATENT DOCUMENTS

| | | |
|---|---|---|
| WO | WO 95/19788 | 7/1995 |
| WO | WO 99/25817 | 5/1999 |
| WO | WO 99/46372 | 9/1999 |
| WO | WO 00/60115 | 10/2000 |
| WO | WO 00/68399 | 11/2000 |
| WO | WO 01/30965 | 5/2001 |
| WO | WO 02/44321 | 6/2002 |
| WO | WO 02/097114 | 12/2002 |
| WO | WO 03/008573 | 1/2003 |
| WO | WO 03/020931 | 3/2003 |
| WO | WO 03/056022 | 7/2003 |
| WO | WO 03/066650 | 8/2003 |
| WO | WO 03/068797 | 8/2003 |
| WO | WO 03/070193 | 8/2003 |
| WO | WO 03/070750 | 8/2003 |
| WO | WO 03/070895 | 8/2003 |
| WO | WO 03/070914 | 8/2003 |
| WO | WO 03/070918 | 8/2003 |
| WO | WO 2004/009792 | 1/2004 |
| WO | WO 2004/065581 | 8/2004 |

OTHER PUBLICATIONS

Cui et al (RecA-Mediated, Targeted Mutagenesis in Zebrafish. Marine Biotechnology,2003. 5:174-184).*

Anderson, (1998). Human gene therapy. Nature 392 (suppl): 25-30.

Ausubel, et al. (1994). *Current Protocols in Molecular Biology*, Contents V. 1, 2, and 3. Table of Contents.

Borelli et al. (1988). Targeting of an inducible toxic phenotype in animal cells. Proceedings of the National Academy of Sciences USA 85: 7572-7576.

Dove (2000). Milking the genome for profit. Nature Biotech. 18: 1045-1048.

Dupuy et al. (2001). Transposition and gene disruption using a mutagenic transposon vector in the male germline of the mouse. Genesis 30: 82-88.

Dupuy et al. (2002). Mammalian germ-line transgenesis by transposition. Proceedings of the National Academy of Sciences USA 99: 4495-4499.

Fischer et al. (2001). Regulated transposition of a fish transposon in the mouse germ line. Proceedings of the National Academy of Sciences USA 98: 6759-6764.

Hackett et al. (1999). Development of genetic tools for transgenic animals. *IN* Transgenic Animals in Agriculture. CAB International, Wallingford, UK. 19-35.

Hackett et al. (2000). The molecular genetics of transgenic fish. Recent Advances in Marine Biotechnology 4: 77-145.

Horie et al. (2001). Efficient chromosomal transposition of a Tc1/mariner-like transposon Sleeping Beauty in mice. Proceedings of the National Academy of Sciences USA 98: 9191-9196.

Horie et al. (2003). Characterization of *Sleeping Beauty* transposition and its application to genetic screening in mice. Molecular and Cellular Biology 23: 9189-9207.

Ivics et al. (1997) Molecular reconstruction of *Sleeping Beauty*, a Tc1-like transposon from fish, and its transposition in human cells. Cell 91: 501-510.

Jaenisch (1988). Transgenic animals. Science 240: 1468-1474.

Marshall (2002). Clinical research. Gene therapy a suspect in leukemia-like disease. Science. 298: 34-35.

Miskey et al. (2003). The Frog Prince: a reconstructed transposon from Rana pipiens with high transpositional activity in vertebrate cells. Nucleic Acids Research 31: 6873-6881.

Montini et al. (2002). In vivo correction of murine tyrosinemia type I by DNA-mediated transposition. Molecular Therapy 6: 759-769.

Muir et al. (2002). Assessment of possible ecological risks and hazards of transgenic fish with implications for other sexually reproducing organisms. Transgenic Research 11: 101-114.

Niiler (2000). FDA, researchers consider first transgenic fish. Nature Biotechnology 18: 143.

Reichardt (2000). Will souped up salmon sink or swim? Nature 406: 10-12.

Verma et al. (1997). Gene therapy—promises, problems and prospects. Nature 389: 239-242.

Verma (2002). Success and setback: another adverse event. Molecular Therapy 6: 565-566.

Vigahl et al. (2002). Common physical properties of DNA affecting target site selection of *Sleeping Beauty* and other Tc1/*mariner* transposable elements. Journal of Molecular Biology 323: 441-452.

Yant et al. (2000). Somatic integration and long-term transgene expression in normal and haemophilic mice using a DNA transposon system. Nature Genetics 25: 35-41.

Yin et al. (2002). RNA-mediated gene regulation system: now and the future. International Journal of Molecular Medicine 10: 355-365.

* cited by examiner

Modified Integrase with DNA Tether

Vector-DNA Tether

Carrier-DNA Tether

Target-Site Modification (Triple Helix)

Target-Site Modification (Stabilized Triple Helix)

Target-Site Modification (Stabilized Triple Helix) with Tethering of Carrier to Stabilizing Agent

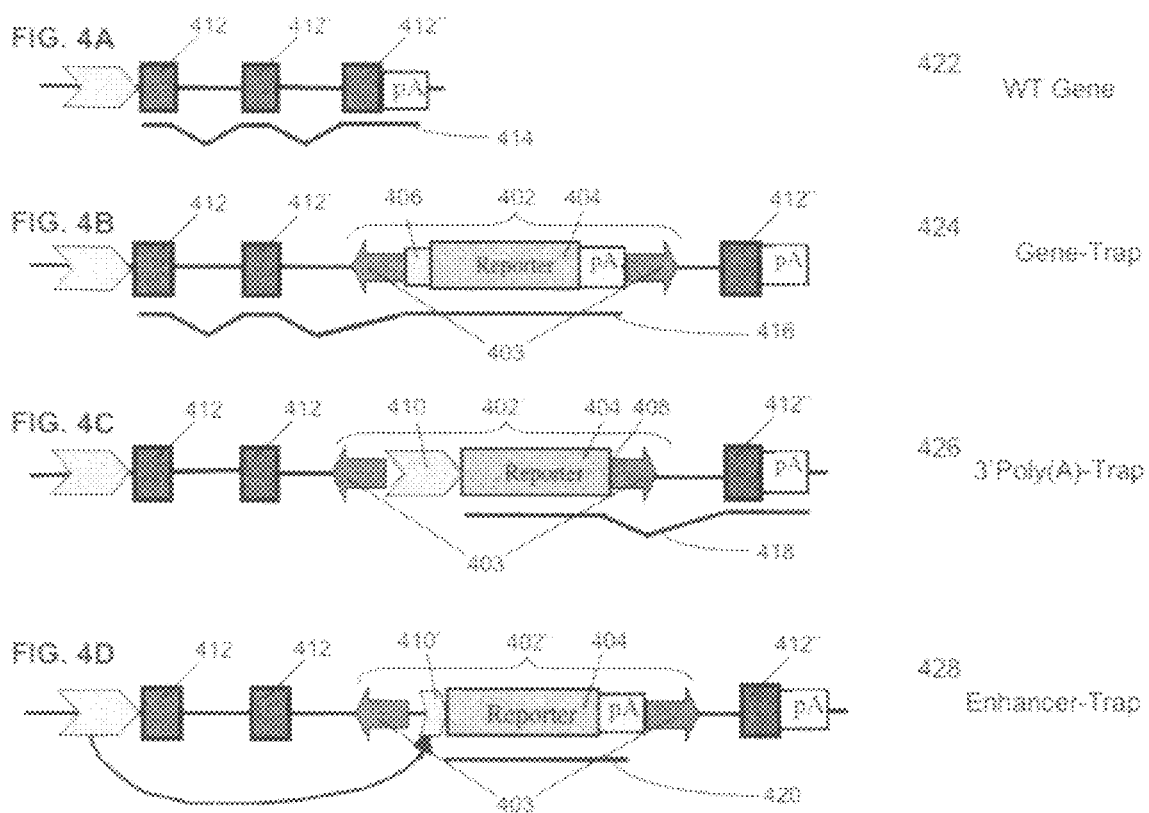

INTEGRATION-SITE DIRECTED VECTOR SYSTEMS

FIELD OF THE INVENTION

The field of the invention is related to insertion of deoxyribonucleic acid (DNA) sequences into a host's DNA, and to site-specific targeting of such integration using targeting molecules that bind to specific target DNAs.

BACKGROUND

Many health problems in a patient can be treated, in principle, by introducing a therapeutic gene into the deoxyribonucleic acid (DNA) of the patient. In particular, many diseases, such as hemophilia as one specific example, can be linked to specific gene defects in individuals that result in conditions of varying severity. Despite many years of intensive scientific and medical work, however, there is no consistently safe and successful way to introduce genes into a patient. The significant issue is that vehicles used to deliver the genes do not insert therapeutic genes into specific sites in a patient's genome. As a result, insertion of therapeutic genes may disrupt the patient's genes to cause cancer or other unwanted effects.

SUMMARY OF THE INVENTION

This application describes materials and methods for inserting genes into a pre-selected site in the patient's genome so that unwanted effects are reduced or eliminated. A molecular tether binds both a carrier and also a preselected site on a patient's DNA so that the carrier is positioned near the target site. The proximity of the carrier to the preselected site results in a therapeutic gene or other desired genetic sequence being inserted at or near the preselected site. The system for inserting the genes involves various components, which are selected according to the general approach that is being used. Regardless of the choice of the various components, it is advantageous to bind the carrier because, unlike the other components, it is possible to bind the targeting molecule to the carrier without compromising the performance of the carrier.

Certain embodiments are a molecular tether comprising a target DNA-binding domain having a specific binding affinity for a first-target DNA segment in a host, a carrier-binding domain that specifically binds to a second-target DNA segment on a carrier, and a spacer covalently bonded to the target DNA-binding domain and the carrier-binding domain. The target DNA-binding domain may comprise a polypeptide and the carrier-binding domain may comprises a second sequence of amino acids. Further, the molecular tether maybe made from polypeptides. Certain embodiments include a nucleic acid segment comprising an mRNA or a DNA encoding the a molecular tether polypeptide.

Certain embodiments are a method for site-directed DNA insertion into a genome, the method comprising inserting, within a cell, carrier DNA and a molecular tether wherein the carrier DNA comprises a vector and a tether-specific motif, and wherein the molecular tether comprises a target-DNA-binding domain connected via a spacer to a carrier-binding domain specific for the tether-specific motif. Certain embodiments include a method of treatment of a patient comprising delivering cells with fully functional genes or other DNA sequences into a patient, wherein the cells have new properties as a result of using a method using a molecular tether.

BRIEF DESCRIPTION OF THE FIGURES

FIG. 3C depicts use of a molecular tether that specifically binds the carrier with a first moiety and uses a second moiety comprising single-stranded sequence-RecA or single-stranded sequence-Rad51to bind the target DNA site;

FIG. 4A depicts a trap construct for inclusion in Sleeping Beauty transposons with site-specific integration;

FIG. 4B depicts a gene-trap;

FIG. 4C depicts a 3'-poly(A) trap; and

FIG. 4D depicts an enhancer-trap.

DETAILED DISCUSSION OF PREFERRED EMBODIMENTS OF THE INVENTION

Introduction

Figure 1:
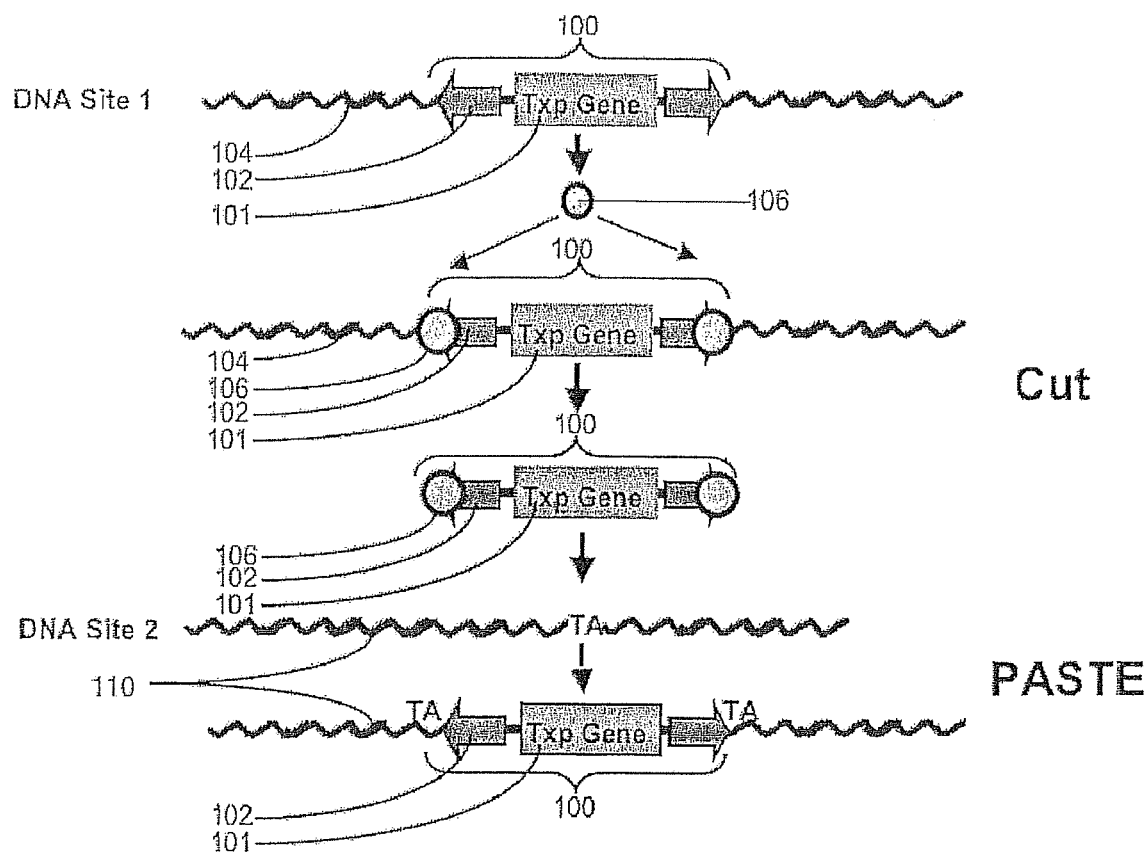
FIG. 1 depicts the cut-and-paste mechanism of transposition for a DNA transposon by an active transposase gene.

Non-viral vectors used to deliver genes into chromosomes of vertebrates generally integrate in a near random fashion into chromatin and many viral vectors integrate into or in the vicinity of transcriptional units. The theoretical possibility of insertional mutagenesis occurring as a result of random integration of a genetic construct has been recognized for many years (e.g., Verma and Somia, 1997, Check, 2003; Linden, 2002; Williams and Baum, 2003). This theoretical possibility was realized when two human patients with severe combined immunodeficiency disorder (SCID)-XI were treated with retroviruses that compensated for the loss of IL2RG. The insertion of a retrovirus carrying a growth promoting genes in the vicinity of the LM02 gene, an oncogene, induced proliferation of T lymphocytes (Marshall, 2002; Verma, 2002; Hacein-Bey et al., 2003). This event occurred because transcriptional regulatory elements can act over thousands of base pairs of chromatin. As a result, to limit the actions of a transgene on genes in genomes, one may either direct the transgene to integrate in sites distal from critical genes and/or block the activities of their transcriptional regulators.

Several ways to avoid the observed problems of random or semi-random integration have been proposed. The first is to use natural site-specific integrases such as the *Streptomyces* ϕC31 phage integrase. This enzyme directs integration of most transgenic constructs into a relatively small number of sites in human chromosomes that resemble its normal recognition site (Groth and Calos, 2004). However, potential problems associated with this integrase, including chromosomal deletions and translocations have compromised the use of this agent. An integrase refers to a protein that inserts a nucleic acid into another nucleic acid, and includes recombinases and various enzymes produced by viruses.

A second strategy to avoid problems associated with random integration is to use border/insulator elements to block enhancers in vectors from activating chromosomal genes (e.g., as set forth in U.S. Publication No. 2004/0203158 and PCT/US2004/00977). A third method is to modify a recombinase or other integrase that normally has random integration activity such that it will bind to a specific site(s) and direct integration into proximal chromatin (e.g., Kaminski et al., 2002, 2005; Yant et al., 2005b, PCT Application WO04009792). There are two problems with this approach. First, each recombinase is site-specific and that modification may compromise its activity of the enzyme. Second, tethering an integrase such as a transposase to a particular region would in theory increase the probability that a transposon could be induced to re-transpose in and out of sites close to the original insertion. As a result, integration efficiency is greatly reduced. A lesser problem is that insertion into any other site requires reconstruction of a new transposase gene and polypeptide that require extensive testing, thereby lowering their commercial usefulness.

These approaches, in the Detailed Description above, involve modifying the vector and/or the integrating recombinase or other integrase. However, by directing the carrier of the integrating vector (e.g., a plasmid carrying a transposon vector) to a chromosomal site using reagents that are independent of the integrating vector and its associated recombinase, site-specificity can be achieved without compromising the vector system. Further, the carrier can be adapted for use with many vectors. Therefore, from a commercial point of view, engineering the non-integrating portion of the carrier saves the time and cost of modifying the targeting system for every integration vector that is used. And, from a safety and a governmental regulatory point of view, once the targeted carrier system is validated, it can be used for any gene delivery into any genome.

Components Related to Delivery of Nucleic Acid Segments

As discussed in detail below, a carrier refers to any molecule that can be replicated and that includes an expression vector. Examples of carriers include any DNA segment with a replicon, e.g., plasmid, phage genome, cosmid, or phasmid into which another nucleic acid segment may be inserted so as to bring about replication of the inserted segment. An insertable nucleic acid segment may be inserted from a carrier into a host's DNA. The insertable nucleic acid segment generally comprises an expressible nucleic acid segment that can be expressed by the cell or equivalent system that receives the inserted segment to provide a therapeutic protein, a marker molecule, a molecule of commercial importance (e.g., erythropoietin from a transgenic animal) or other molecule (e.g., a functional RNA moiety, which would include an siRNA or shRNA that can regulate expression of genes). The inserted nucleic acid segment will typically contain an expression vector that contains the expressible nucleic acid and also at least one expression control sequence. An expression control sequence is a DNA sequence that controls and regulates the transcription, RNA processing and/or translation of a DNA or RNA sequence.

A vector is a broad term that includes any specific DNA segment that is designed to move from a carrier into a target DNA. Most vectors will contain an expression cassette that comprises transcriptional regulatory and processing motifs/signals and/or a gene or other functional RNA molecule. A vector may be referred to as an "expression vector", or a vector system, which is a set of components needed to bring about DNA insertion into a genome or other targeted DNA sequence such as an episome, plasmid, or even virus/phage DNA segment. Vector systems such as viral vectors (e.g., retroviruses, adeno-associated virus and integrating phage viruses), and non-viral vectors (e.g., transposons) used for gene delivery in animals have two basic components: 1) a vector comprised of DNA (or RNA that is reverse transcribed into a cDNA) and 2) a transposase, recombinase, or other integrase enzyme that recognizes both the vector and a DNA target sequence and inserts the vector into the target DNA sequence.

The term molecular tether is a broad term that includes any molecule that acts to bring together two separate nucleic acid segments. Molecular tethers can be used to increase the frequency that a vector will be integrated, e.g., by an appropriate recombinase/integrase/transposase, into a target DNA at or around a specific site or family of sites in a genome, chromosome or other DNA molecule. Molecular tethers may be polypeptides that may or may not be covalently fused to a nucleic acid molecule. A tether may be comprised of two DNA-binding motifs separated by a spacer, e.g., a polymer or a peptide. The DNA-binding motifs may have nucleic acid sequence specificity, for example, by zinc fingers, helix-turn-helix, helix-loop-helix, homeodomain segments or a specific nucleic acid sequence. DNA-binding motifs may bind specifically to a nucleic acids through the use of a target-specific single stranded DNA sequence provided with the vector system along with a protein to stabilize corresponding triple helices (e.g., the bacterial RecA protein or the eukaryotic Rad51protein), as described in detail, below.

Transposon Vectors

Transposons or transposable elements comprise a section of nucleic acid sequence bounded by repeat sequences. Active transposons encode, along with other proteins, transposase enzymes that facilitate the insertion of the nucleic acid into DNA sequences. These transposable elements transpose through a cut-and-paste mechanism; the element-encoded transposase catalyzes the excision of the transposon from its original location and promotes its reintegration elsewhere in the genome. A transposase protein is capable of binding to DNA at sequences termed inverted terminal repeats. Transposons typically contain at least one, and sometimes two, sets of inverted repeats that respectively flank an intervening nucleic acid sequence. The transposase binds to recognition sites in the inverted repeats and catalyzes the incorporation of the transposon into genomic DNA, generally at repeat sequences representing transposon insertion sites.

An example of a vector system is shown in FIG. 1 where a Sleeping Beauty transposase 106 cuts a transposon 100 out of a carrier DNA molecule 104, e.g., a carrier plasmid, and inserts transposon 100 into chromosome 110. Sleeping Beauty transposon 100 and corresponding transposase 106 are from an archaic transposon that was engineered to reactivate the transposon to function in vertebrates. FIG. 1 depicts the cut-and-paste mechanism of transposition for DNA transposon 100 with an expressible nucleic acid segment 101 such as a therapeutic gene, a gene encoding a protein of commercial importance, or marker. The inverted arrows 102 depict the only DNA sequences required by the transposase for transposition.

For commercial use, a therapeutic gene, a gene encoding a protein of commercial importance, or sequences therefore could be, for example, a protein or an RNA molecule (from Hackett et al., 2005). Additional aspects of the Sleeping Beauty system are set forth in U.S. Pat. No. 6,489,458 and U.S. patent Ser. No. 09/191,572 entitled "Nucleic Acid Transfer Vector For The Introduction Of Nucleic Acid Into The DNA Of A Cell"; Ser. No. 09/569,257 entitled "Vector-Mediated Delivery Of Integrating Transposon Sequences"; Ser. No. 10/128,998 entitled "Transposon System For Gene Delivery In Vertebrates"; and Ser. No. 10/128,998 "Composition For Delivery Of Compounds To Cells"; see also PCT application WO 99/25817, entitled "Nucleic Acid Transfer Vector For The Introduction Of Nucleic Acid Into The DNA of a Cell", PCT Application WO 00/68399 "Vector-mediated delivery of integrating transposon sequences". Other transposon systems have been tested in vertebrates, including Tc1 from nematodes, Mos1, Himar1 and piggyBac from insects, the hAT transposon Tol2 from medaka, Frog Prince, and the L1 retrotransposon from humans that have been examined as vectors in human and/or other vertebrate cells (e.g., Fischer et al., 2001; Ding et al., 2005; Koga et al., 2003; Miskey et al., 2003, Han and Boeke, 2004).

An advantage of a transposon system for human gene therapy is that it avoids viruses. Viruses have been associated with most of the adverse events that have occurred in gene therapy (Thomas et al., 2003; Hackett et al., 2005; Essner and Hackett, 2005). Genes delivered into the livers of mice using the Sleeping Beauty Transposon System can partially restore deficiencies of several enzymes, including those for blood clotting that are missing in some hemophilia patients and murine tyrosinemia type I (e.g., Yant et al., 2000; Montini et al., 2002; Ohlfest et al. 2005a; Patent WO 01/30965) as well as treat cancer by gene therapy (Ohlfest 2004, 2005b). This work is being extended to other genes for other diseases (Hackett et al., 2005).

Some aspects for successful gene therapy relate to 1) finding the appropriate gene for transfer, 2) find a method for delivery of the gene to the tissues that are affected or to other tissues that can provide the necessary activity from afar, and 3) achieving long-term expression of the transgene so that repeated deliveries are not required. 4) Reliable and safe methods should be used. As noted earlier, there is a concern about random or otherwise non-targeted gene delivery (Engelman, 2005). Consequently, it is felt that targeting is desirable. It has an appeal from a regulatory point of view and theoretically at least it might result in predictable regulation (Glover et al., 2005; Mok and Lever, 2005). Similar concerns exist for transgenic animals (Hackett et al., 1999; Wall, 2001; Fletcher et al., 2004).

As already indicated, it is advantageous to target the integration of DNA to a specific DNA site without modifying the vector or integrating enzyme. While other types of vectors can successfully make use of the targeting approach described herein, Sleeping Beauty transposon system (U.S. Pat. No. 6,489,458) is used as a specific example in the detailed discussion below. The Sleeping Beauty System is synthetic (Ivics et al., 1997) and was the first vertebrate transposon system specifically designed to integrate transgenic DNA into chromosomes. A Sleeping Beauty transposon plus Sleeping Beauty transposase comprise the Sleeping Beauty transposon system. One or both components of the Sleeping Beauty system may be delivered in vivo or ex vivo to cells as portions of a vector, e.g., the transposon gene and/or the transposase gene. When the transposase is present in the cell, it can cut the transposon out of the plasmid carrier for reinsertion into a chromosome. The Sleeping Beauty transposase gene may or may not be on the same plasmid carrier as the transposon. Alternatively, an mRNA encoding the transposase function may be used as an alternative to the delivery of the transposase gene for integration into the genome and subsequent expression. More generally, an integrating vector like a transposon or other vector is part of a carrier, e.g., a plasmid. In certain embodiments of the invention, it is the carrier molecule that is used to target insertion of a vector to specific site(s) in chromosome(s).

Most viral integrases and transposases do not require a specific sequence in the target DNA for integration. Many of the integrating vectors used for introducing foreign DNA into chromosomes require some recognition signal. The commonly used retroviruses and lentiviruses, as well as adeno-associated virus (AAV), show varying degrees of preference for transcriptional units and/or their proximal promoters (Schroder et al., 2002; Wu et al., 2003, 2005; Nakai et al., 2003; Mitchell et al., 2004; Maxfield et al., 2005; Holman and Coffin, 2005; Yant et al., 2005a). In contrast, Sleeping Beauty transposase recognize a simple DNA sequence, TA, (TA) sequence, but depending on the deformability of the flanking sequences, Sleeping Beauty transposase shows more than 10-fold preference for some sites over others (Liu et al., 2005). In contrast, the *Streptomyces* φC31 phage integrase has a requirement for a 34-39-basepair att sequences in its host, but shows a degenerate pattern of integration in mammalian cells (Groth and Calos, 2004; Groth et al., 2000; Olivares et al., 2002).

Methods of Guiding Integration of Transgenic Vectors to Specific Target Sites

Figure 2A:
FIG. 2A depicts direction of a vector to a target DNA segment by modifying an integrase/recombinase by use of a molecular tether that links an integrase/recombinase to the target site.

FIG. 2 depicts three methods for guiding an integrating vector (e.g., a transposon or other DNA sequence that has a recombinase/integrase-recognition sequence), contained in a carrier (e.g., a plasmid) from which the vector is excised for introduction into a chromosome. FIG. 2A shows the components of vector system 200 having carrier 201 and target chromosome 202. The first method of guiding integration of expression vector 203 having expressible nucleic acid segment 205 is to attract the recombinase/integrase enzyme(s) 204 to particular regions 206 in the chromosome near target site 207 via tether 208. The tether 208 has DNA-binding domain 210 that binds target site 207 and is attached to spacer 212 that is joined to the recombinase/integrase protein molecule 204. Tether 208 thus has three domains: a target DNA-binding-domain 210 that will bind to a particular DNA sequence such as target site 207 (e.g., a cluster of zinc finger motifs that bind to target site 207), a spacer 212 that reduces the interference of the DNA-binding domain with recombinase/integrase enzyme 204 activity.

Figure 2B:
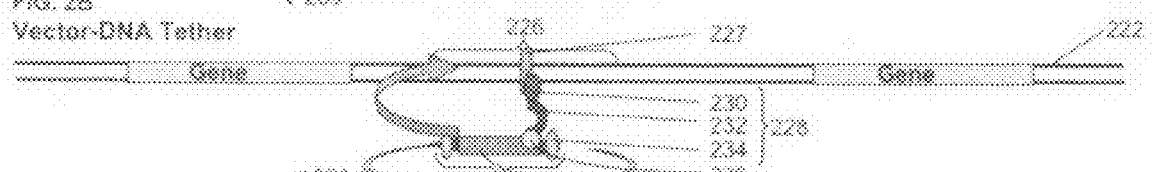
FIG. 2B depicts a molecular tether between a vector and a target DNA segment.

It has been reported elsewhere that a transposon has been used with a chimeric protein that comprised a transposase and zinc fingers that bind to a target site on the host DNA (e.g., see Yant et al., 2005b; Kolb et al. 2005, Coates et al., 2005; PCT Application WO04009792). A problem with this approach, however, is that the functioning of the transposase is hindered by its inclusion in the chimera, or placement of the transposase at the target site could lead to multiple rounds of excision-reintegration in a local region of the target site. This could have a chance of introducing unwanted, and difficult to detect, mutations from 'footprints' where excision occurred. FIG. 2B depicts a second strategy, shown with system 220, which includes carrier 221, having expression vector 223 and expressible nucleic acid segment 225, with tethering molecule 228 having target DNA-binding-domain 230 to specifically bind to a target segment 227 in region 226 on host's chromosome 222. In this strategy, tethering molecule 228 is made up of two DNA-binding domains joined by spacer 232, the first being 230 similar to 210 described above, wherein it binds to a target-DNA segment 227. The tethering molecule 228 has a second DNA-binding domain 234 that will bind a region 236 in expression vector 223. As with the first approach, however, binding expression vector 223 can have adverse results. However, this approach is still advantageous with respect to the approach in FIG. 2A since the transposase, or generally a corresponding integrase, is not modified to introduce a second DNA-binding site, so that the transposase's fully functional form can be used.

Figure 2C:
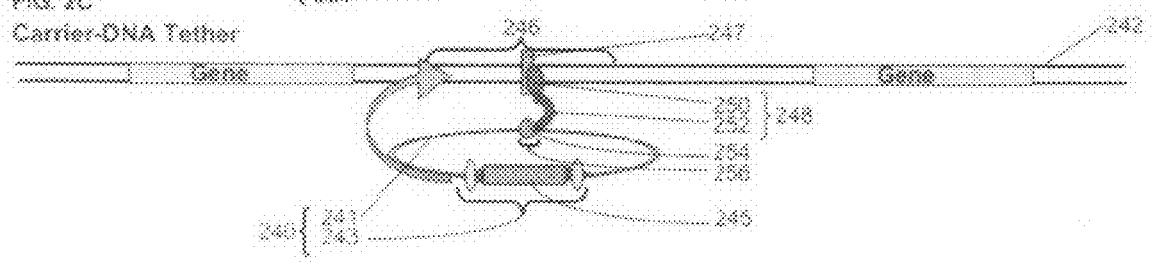
FIG. 2C depicts a molecular tether between a carrier and a target-DNA segment, with the carrier being bound at a portion that does not contain a transposon or expression cassette.

A third strategy in FIG. 2C is shown using system 240, which includes carrier 241, having expression vector 243 and expressible nucleic acid segment 245. Tethering molecule 248 has specific binding portion 254 connected via spacer 252 to domain 250. Domain 250 specifically binds to target segment 247 in region 246 on host's chromosome 242 to attract carrier molecule 241 (e.g., a plasmid in which the vector is embedded) to the target site. This may be achieved using a double DNA-binding-domain tethering molecule similar to the second strategy, but with the advantage that the expression vector itself is not directly linked to a site. Thus, specific binding portion 254 is directed to a portion 256 of the carrier that is not the expression vector or is not the expressible nucleic acid segment. An advantage of this approach is that once the expression vector is cleaved from the carrier, it no longer has any association with the polypeptide tether. Examples 6 and 7 provide additional details related to this strategy.

The molecular tether, by bringing the carrier of a vector system, e.g., a transposon, into proximity to a targeting sequence, may thus embody part of an integration-site specific integration system or method.

Embodiments of molecular tethers generally comprise a spacer joined to at least two target-binding moieties. The targeting molecules may be isolated or in a mixture with a carrier(s) and/or target DNA. In some embodiments, the targeting molecules are reacted with at least one type or genus of carrier, and unbound targeting molecules and/or carriers are removed from the mixture by a purification step, e.g., based on size, molecular weight, or charge.

In general, the spacer can be selected to provide appropriate bonding between the two DNA binding moieties. The length and chemical nature of the spacer can be selected such that the functionality of the DNA binding moieties is not altered beyond acceptable limits and similarly that the DNA insertion efficiency also is not altered beyond acceptable limits. While longer linkers may be desirable with respect to reducing any interference between the DNA binding sites, if the linker is too long, the specificity provided by the targeting molecule may be reduced also. A person of ordinary skill in the art can balance these parameters as desired.

A spacer for a targeting molecule may be a peptide. Peptide, or polypeptide, is a term that refers to at least three amino acids joined to each other, and includes polypeptides and proteins. Alternatively, a spacer may be a polymer, e.g., polyethylene oxide, or a relatively small molecule that joins the polypeptide binding moieties. A range of options is available based on the skill in the art.

It is generally desirable to use covalent bonding between the linker and two binding moieties. If both DNA binding moieties comprise polypeptides, the linker can be similarly a polypeptide. The formation of protein chimera is well established. Specifically, a polypeptide linker can be engineered such that the entire linker molecule is expressed simultaneously or they can be engineered for chemical linkage at suitable C-terminal and N-terminal sites. The formation of fusion protein is described further, for example, in U.S. Pat. No. 5,985,575 to Wickens et al., entitled "Tethered Function Assay For Protein Function," incorporated herein by reference.

More generally, other poly-functional linkers can be designed to react with specific functional groups in respective DNA specific binding moieties. These other linkers can be bonded to the terminal sites of polypeptide binding moieties or with side chains. For example, suitable approaches using either disulfide bridges with a 5-methyl-2-iminothiolane linker or dialdehydes, such as gluteraldehyde, are specific examples of poly-functional linkers for bonding with protein DNA binding moieties. The bonding of polymers to proteins through disulfide bonds or through amide bonds is described, for example, in U.S. Pat. No. 6,410,017 to Weisgerber et al., entitled "Personal Care Compositions Containing Active Proteins Tethered To A Water Insoluble Substrate," incorporated herein by reference. In general, a person of skill in the art can select suitable bifunctional linker for chemical bonding to available functional groups of the DNA binding moieties.

Moieties of a molecular tether intended to specifically bind to other molecules are referred to as target-binding moieties. Target-binding moieties include, for example, target DNA-binding domains, carrier-binding domains, and binding domains that specifically bind a portion of a vector system besides a carrier. Certain embodiments thus involve a targeting molecule comprising at least two target-binding moieties. The targeting molecule may have a spacer that joins the target-binding moieties.

A target DNA-binding domain is a target-binding moiety that specifically binds a target DNA. Examples are described, below, and include, for example, antibodies, a zinc finger, RecA, Rad51 protein, and a RecA- or Rad51-coated DNA segment that hybridizes to the host DNA target site.

The carrier-binding domain is a target-binding moiety that specifically binds a carrier. The carrier-binding domain of may bind any portion of the carrier, including the expression vector, or may bind only the non-vector portions of the carrier. Examples of carrier-binding domains are described, below, and include, for example, antibodies, a zinc finger, or other DNA-binding motifs. A domain on the carrier can be specifically engineered to have particularly high binding affinity for a corresponding carrier binding domain since the non-vector portion of the carrier is not related to function of the integrated portion of DNA following integration and likely will be lost after integration.

A target-binding moiety may be made to specifically bind any portion of a carrier. However, it is anticipated that binding of a targeting moiety to a portion of the vector sequences, e.g., inverted terminal repeats on transposons, may be undesirable in some embodiments.

Specific binding is a binding to a particular target with a much greater affinity than to non-target molecules. Specific binding generally involves a plurality of non-covalent interactions, such as electrostatic interactions, van der Waals interactions, hydrogen bonding, and the like. Specific binding interactions characterize antibody-antigen binding, enzyme-substrate binding, and specific binding in protein-receptor interactions. In the case of single-stranded nucleic segments, specific binding takes place between complementary strands. In certain embodiments, specific binding to double-stranded target DNA takes place when a moiety specifically recognizes and binds to the double stranded target DNA. In some embodiments, the double-stranded DNA is opened up into a new configuration, such as a triple helix, as part of the specific binding event. For instance, RecA in combination with a single-stranded targeting DNA sequence is used to specifically bind to a double stranded DNA target segment in a host—the RecA "stabilizes" the triple helical structure produced by a single-stranded DNA sequence that is complementary to the double-stranded DNA target segment.

A target-binding moiety may comprise a moiety that comprises a zinc finger. The zinc finger may be used to specifically target a target DNA segment. Zinc finger protein domains bind with specificity to double stranded DNA. Zinc finger domains have been identified in thousands of putative transcription factors with over 10,000 zinc finger sequences. A zinc finger domain is about 30 amino acids in length, which are thought to fold into an alpha helix with two invariant histidine residues and a beta turn with two invariant cysteine residues. The beta turn and alpha helix seem to be held in a particular confirmation due to the invariant histidine and cysteine residues. An exemplary motif for a ($C_2H_2$) class zinc finger is -Cys-$(X)_{2-4}$-Cys-$(X)_{12}$-His-$(X)_{3-5}$-His, where X is any amino acid., but there are many variations of zinc-organizing amino acid motifs that are used in transcription factors (Pabo and Sauer, 1992; Sanchez-Garcia, and Rabbitts, 1994).

It is thought that each zinc finger domain recognizes a three-nucleotide DNA sequence, and may contact the DNA at three or four nucleotides. The zinc fingers interact with the DNA through amino acid side chains. Selection or design of specific binding zinc fingers have focused on four amino acids that can be specified as −1, +2, +3, +6 relative to the starting position of the alpha helix. Design methods for selecting zinc finger sequences are described further in U.S. Pat. No. 6,794,136 to Eisenberg et al., entitled "Iterative Optimization In The Design Of Binding Proteins," incorporated herein by reference. Another approach to design of zinc fingers with desired DNA specificity is described in published U.S. Patent Application 2005/0037385A to Choo et al, entitled "Nucleic Acid Binding Proteins," incorporated herein by reference. The zinc finger domains are connected in native proteins with polypeptide linkers. The formation of chimeric proteins with engineered linkers is described in U.S. Pat. No. 6,903,185 to Kim et al., entitled "Poly Zinc Finger Proteins With Improved Linkers," incorporated herein by reference. Chimeric proteins with larger numbers of zinc fingers and corresponding greater selectivity can be designed based on the disclosures in these patents. Most zinc fingers recognize 3 basepairs so that for a unique signal in the genome of a vertebrate, a 16-basepair ($4^{16} > 6 \times 10^9$) sequence is sufficient for targeting. Such a sequence can be specified by six zinc finger motifs. Thus, for most purposes we would use six or more zinc fingers, with the "extra" fingers providing security that the correct sequence is chosen (e.g., Beerli et al., 2000; Urnov et al., 2005; Bae et al., 2003; Bibikova et al., 2003).

In addition, a target-binding moiety may comprise a synthetic polyamide. The synthetic polyamide may be used to specifically identify and bind to a target DNA segment. Synthetic polyamides have been proposed as DNA binding compounds with sequence specific specificity. These polyamides comprise N-methylpyrrole and N-methylimidizole amino acids. These synthetic DNA binding molecules are described further in U.S. Pat. No. 6,555,692 to Dervan, entitled "Preparation And Use Of Bifunctional Molecules Having DNA Sequence Binding Specificity," incorporated herein by reference.

A target-binding moiety may include a moiety that induces deformation of a target site. Indeed, the preference of integrases and transposases for deformable DNA may advantageously be used. Many recombinase/integrase molecules have a preference for 'deformable' DNA (Rao et al., 2000; Bushman, 2002; Vigahl et al., 2002; Liu et al., 2005; Wu et al., 2005). Deformable DNA has a malleable structure that is different from the common B-form DNA associated with most natural DNA sequences. Consequently, a method for site-specific integration of vectors having recombinase/integrase molecules is to deform a target site. This method can be practiced by introducing a triple helical conformation via an oligonucleotide such as a complementary DNA or a complementary morpholino (e.g., Rao et al., 2000; Basye et al., 2001; Igoucheva et al., 2004).

Figure 3A:
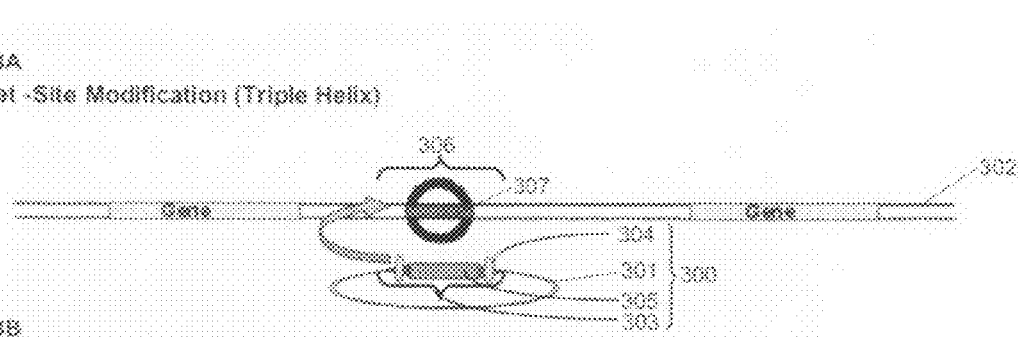
FIG. 3A depicts deformation of the target DNA site by a triple-helix-forming oligonucleotide or analog.
Figure 3B:
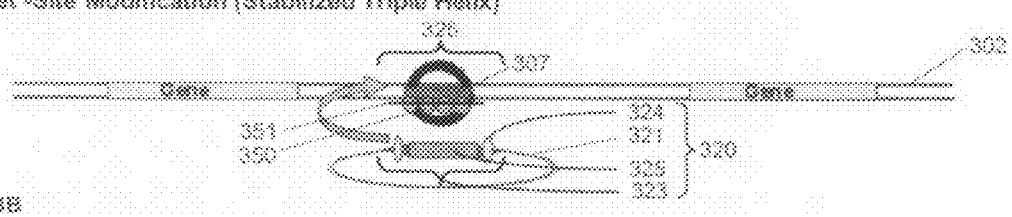
FIG. 3B depicts addition of an oligonucleotide complementary to the target site in combination with a triple-helix-stabilizing protein such as RecA or Rad51.
Figure 3B:
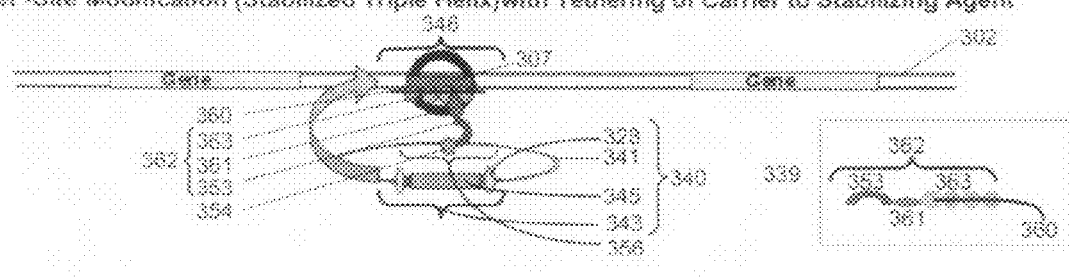

FIG. 3 depicts a use of target-binding moieties that deform target sites, wherein vector systems 300, 320, 340 having carriers 301, 321, 341 deliver expression vectors 303, 323, 343 and expressible nucleic acid segments 305, 325, 345 to regions 306, 326, 346 near a target site on host chromosome 302 having a target DNA segment 307. Vector systems 300, 320, and 340 having binding sites for transposase enzymes 304, 324, and 328.

Referring to FIG. 3A, the deformed target DNA segment 307 is shown as a triple-helix structure, and the structure may be created in the presence of a complementary strand of the double-stranded DNA (not shown).

FIG. 3B depicts a variation on this theme, wherein the triple helix can be stabilized by protein 350 such as *E. coli* protein RecA or eukaryotic Rad51 protein in combination with the complementary strand of DNA 351 for the target DNA site 307 (e.g., see Cui et al., 2003). The opening up of the host's double-stranded DNA to a triple-helix structure allows for the carrier or a molecular tether associated with the carrier to specifically bind to the host's target DNA segment. Optionally, DNA segment 351 may be part of a molecular tether.

Alternatively, FIG. 3C depicts RecA proteins used as a molecular tether when a DNA-binding domain is introduced. Molecular tether 362 is shown in isolation at 339 and in association with other parts of the system at 340. Molecular tether 362 has RecA 363 connected to spacer 361 which is also attached to carrier-binding domain 353 that specifically binds to a binding site 354 on carrier 341. Site 354 is disposed on portion 356 of carrier 301 that is not the expression vector 343. The molecular tethering may be, e.g., to the carrier or vector DNA, and, a RecA-tether to the expression vector itself could also be made and used. DNA 360 complementary to the DNA target segment 307 can be exposed to a molecular tether 362 having a RecA target-binding moiety 363 so that the RecA 363 binds the complementary DNA 360 and will thereby specifically bind to the target DNA 307 to thereby localize carrier 341 to region 346 at or near the target DNA sequence 307. Examples 1, 2, 3, and 5 provide additional detail with respect to these approaches.

In another embodiment, the carrier DNA is directed to a selected site or multiplicity of sites in the target DNA via a RecA-LexA hybrid protein that will bind both a triplex-forming oligonucleotide directed to a specific site or family of sites (e.g. an alpha globin pseudogene or the MER family of repetitive elements) and a lexA-binding domain on the carrier (FIG. 3C). In this embodiment, a single-strand of DNA that is uniquely complementary to a single sequence in the genome or a family of repeated sequences is chosen. The single-strand can be to either of the complementary strands of the double-helical DNA target site. When the single-stranded DNA is complexed with RecA, or a related protein like Rad51, the complex is able to base-pair with the DNA double helix by a process that is poorly understood. Significantly, the targeting oligonucleotide provides the specificity for the sequence and the molecular tether comprised of (a) RecA (or Rad51) that binds to the specific site (or sites if a repetitive element is selected as the target) and (b) a carrier-recognition motif (zinc finger, etc.).

Such a molecular tethering molecule thus becomes a universal molecular tether for a specific class of carriers. The universal tethering molecule has at least one target-binding moiety that can bind to a common portion of the carriers in the class, for example it may bind to a target DNA that can be associated with all carriers of the class. The universal tethering molecule also may have RecA or an analogous protein serving as a target-binding moiety for binding a target-DNA in a host chromosome. The RecA binds to a single-stranded DNA segment having a sequence that is complementary to the target-DNA sequence and by creating a triple-helix structure with the target DNA segment in the host chromosome. The carrier then provides an expression vector at the site of the triple helix. The molecular tether is thus universal because, on one portion, any insertable sequence can be put into a carrier that specifically binds the universal molecular tether; and, on another portion, the molecular tether may have a RecA or comparable protein that can be combined with any DNA segment to target the tether to a particular DNA segment. The carrier can include any vector (e.g., a transposon containing any expression cassette, e.g., a therapeutic gene) for integration into a genome in the vicinity of any target sequence because the target sequence is specified by an oligonucleotide that can be constructed for any desired locus (loci) in a genome.

RecA is a bacterial protein that functions in the area of DNA repair and genetic recombination (Cui et al., 2003). Without wanting to be limited by theory, it is thought that RecA combines with single-strand DNA to form an association that "travels" along double-stranded DNA until it "finds" a complementary sequence to the single-strand DNA, at which point the RecA "stops" and, with the single-stranded DNA, forms a triple-helix type structure with the double-stranded DNA. RecA is thus eminently suited to the targeting mechanisms discussed herein because it allows any DNA to be targeted by using RecA in combination with a DNA segment that is similar to the target DNA sequence or the complement of the target DNA sequence.

RecA from *E. coli* has been characterized extensively. RecA associates with single-stranded DNA to form a construct referred to as a 'RecA filament'. In the presence of ATP, a RecA filament associates with homologous sequences of double-stranded DNA. At the homologous DNA site, a three-stranded D-loop structure is formed with the RecA filament paired with the complementary strand of the double-stranded DNA structure. Thus, the RecA filament provides a specific binding site for a targeting molecule. The binding of a linker to the RecA protein can be used for the formation of a targeting molecule. RecA proteins are described further in published U.S. Patent Application 2004/0224336A to Wagner, entitled "RecA-Assisted Specific Oligonucleotide Extension Method For Detecting Mutations, SNPS And Specific Sequences," incorporated herein by reference and U.S. Pat. No. 6,809,183, entitled "RecA Proteins," incorporated herein by reference.

Rad52 and Rad51 class of proteins are involved in DNA repair in eukaryotes. ScRad51 from yeast has been shown to repair breaks in double-stranded DNA through homologous recombination. ScRad51, as with RecA, polymerize on double-stranded DNA to form a helical fragment. ScRad51 has some sequence homology with RecA, and both proteins have two conserved ATP binding motifs. Other related proteins have been identified, such as MmRad51 in the mouse. Rad51 proteins are described further in U.S. Pat. No. 6,057,104 to Hasty, entitled "Disruption Of The Mammalian Rad51 Protein And Disruption Of Proteins That Associate With Mammalian Rad51 For Hindering Cell Proliferation," incorporated herein by reference and in U.S. Pat. No. 6,576,759 to Zeng et al., entitled "Antisense Inhibition Of Rad51," incorporated herein by reference. In general, members of these classes of related proteins can be effective to stabilize triple stranded DNA sites for use in targeting the DNA genome. Engineered forms of Rad51 are described, for example, in U.S. Pat. No. 6,720,478 to Mahajan et al., entitled "Rad51-Like Polynucleotide And Uses Thereof," incorporated herein by reference.

Embodiments of targeting molecules thus include, for example, bidirectional linker polypeptides with two distinct DNA-binding domains (DBDs), which can be double-stranded DNA. One of the DNA-binding domains will recognize and bind to a sequence in or proximal to an integrating vector or expression vector. The other DNA-binding domains recognize and bind to a sequence at a particular site, or family of sites, in a target DNA segment, chromosome, or genome. The DNA-binding domains may be composed of zinc fingers (Evans and Hollenberg, 1988; Desjarlais and Berg, 1992; or other DNA-recognition motifs such as, but not limited to, helix-turn-helix, helix-loop-helix, or homeodomain sequences (Ptashne, 1988; Schleif, 1988; Struhl, 1989; Pomerantz et al., 1995). A DNA-binding sequence may be natural or synthetic and may be naturally present in the animal or cell that receives the exogenous sequence or it may be non-native to the animal or cell. DNA-binding motifs such as zinc fingers, helix-turn-helix, helix-loop-helix, and homeodomain sequences, to name a few, contain stretches of a few amino acid residues that can extend into either the major or minor groove of a DNA double helix and thereby form ionic bonds with base pairs that comprise a specific sequence that is recognized by the motif (Pabo and Sauer, 1992). For example, most zinc fingers recognize 3 basepairs so that for a unique signal in the genome of a vertebrate, about $6 \times 10^9$ basepairs, one would need to specify a sequence of about 16 basepairs ($4^{16} > 6 \times 10^9$) that could be accounted for by 6 zinc finger motifs. The same logic can be applied to the other DNA-binding motifs.

Embodiments of target-binding moieties also include DNA-distortion elements such as complementary DNA and DNA-analog oligonucleotides (e.g., morpholino, protein nucleic acid, phosphorothioate oligonucleotides) that form localized triple-helical DNA. The embodiments include linker polypeptides consisting of a DNA-binding domain attached to a polypeptide associated with distortion of a DNA double helix (for example the *E. coli* RecA protein or a vertebrate Rad51 protein). The DNA-distorting proteins may function in conjunction with a stabilizing polypeptide to which the linkers can bind.

The molecular tether may have more than one target-binding site, at the target-binding end of the tether, such that more than one site in a chromosome could be selected. In some embodiments, a range of target-binding sites would be between 1 and 20. One advantage of targeting multiple targets is that some targets may occur relatively infrequently, so that choosing more than one target creates a better likelihood of finding a target. The number of moieties may thus be chosen to achieve the desired probability of binding to the intended target DNA in light of the availability of the target DNA in the host and its binding affinity for the moieties. More than one target DNA and/or targeting moieties may be chosen, for example to adjust the odds of binding a target DNA. In some embodiments, a protein is decorated with multiple target-binding moieties. In other embodiments, multiple target-binding moieties are joined to a polymer, e.g., by reacting activated sites on the polymer with precursors to the moieties.

A target site in a genome is predetermined by the engineer of the system, and may be chosen to have a sequence that is present near insertion regions target DNA that provide little or no disruption to gene expression upon insertion of the exogenous vector DNA. In the specific case of SB transposon vectors, remobilization from a carrier DNA into a genome is likely over a sequence of about 100 kb (Dupuy et al., 2001, 2002; Horie et al., 2001, 2003). Thus, for targeted disruption of a gene, a site near the center of a transcriptional unit would be chosen; for targeted insertion of a gene with minimal damage to a genome, one of the "gene deserts" in the genome would be chosen. Either type of site can be found using the available genomic sequence maps (e.g., Lander et al., 2001; Venter et al., 2001).

In some embodiments, the target DNA is a low repetitive element [e.g., L32 ribosomal protein pseudogenes (Venter et al., 2001). Alternatively, other embodiments are directed to more highly repetitive elements such as the Zaphod sequences of which there are about 13,000 in the human genome (Venter et al., 2001; Lander et al. 2001). The advantage of targeting more sequences is two-fold. First the efficiency of delivery is increased because there are many more targets, and thus the integration reaction is more frequent because an appropriate site can be found. Second, off-targeting effects should be lower due to increased integration into correct sites.

The insertable expressible nucleic acid segment can encode or otherwise provide a therapeutic protein, marker molecule, or other molecule. Examples of therapeutic proteins include factors for treating Fanconi anemia, Factor VIII or Factor IX clotting factor genes for treatment of Hemophilias A and B, respectively, proteins for treating lysosomal storage diseases such as iduronidase and b-glucuronidase deficiencies, the CFTR product to treat cystic fibrosis, etc. Therapeutic factors include, for example, proteins that are absent from, or not adequately expressed in the host. Therapeutic factors also include, for example, factors that block other factors in the host. As a specific example, antisense DNA may be expressed in the host to reduce the expression of unwanted factors by the host. Antisense and shRNA expression cassettes are favored genetic tools for insertion into T-cell stem cells to prevent spread of HIV and the onset of AIDS (e.g., Strayer et al., 2005).

Marker molecules include, for example, those molecules that are detectable upon expression. Many experimental regimens benefit from marker molecules used in vivo in experimental animals or in vitro cell cultures for identification of transfected cells. Examples of marker molecules are fluorescent proteins, Green Fluorescent Protein, b-galactosidase, secreted alkaline phosphatase, luciferase and chloramphenicol acetyltransferase.

Vectors and targeting molecules set forth herein may be prepared for a variety of applications, including medical, commercial, scientific, research, experimental, and reagent uses. Medical uses require suitable quality control, verification, and purification standards be met. Preparations may be made for sale as reagents for experimental uses, e.g., through a scientific catalog sales outlet. The vectors and targeting molecules are thus suited to in vivo, ex vivo, and in vitro applications in cell culture systems, artificial cell culture systems, and other in vitro applications.

Certain embodiments of integration systems described below pertain to the Sleeping Beauty transposon system specifically and other integrating systems such as viruses generally. Various exemplary teachings show how to direct integrating vectors to particular sites in genomes by modifying the vectors. These modifications can be made by standard procedures used for constructing recombinant DNA molecules (e.g., Ausubel, 1994). One difference between non-viral and viral vectors primarily concerns introduction of the vector into cells.

Some embodiments of carriers relate to plasmid that incorporate a Sleeping Beauty transposon. The transposon includes an expressible nucleic acid segment. Certain embodiments of plasmid vectors comprise a protein-binding motif (e.g., lexA or Gal4 site) in the backbone of the plasmid that carries the transposon. The carrier can thus be tethered to a unique signal double-stranded DNA sequence in the human genome, e.g. alpha globin pseudogene (Hardison, 1986; Venter et al., 2001) by a designer zinc finger-binding polypeptide that has precise targeting ability (e.g., Urnov et al., 2005).

In another embodiment, a vector, e.g., a Sleeping Beauty transposon carries a therapeutic gene (e.g., Factor VIII or Factor IX clotting factor genes for treatment of hemophilias A and B, respectively) for treatment of humans. Targeting by either of the mechanisms described herein can keep the therapeutic construct from causing adverse events due to integration in or near a critical gene in the human genome. Therapeutic genes are subsequently expressed in the host without causing any damaging disruption of native function.

In another embodiment, a vector, e.g., a Sleeping Beauty transposon carries a commercial gene (e.g., encoding clotting factors) for delivery into an animal bioreactor. The targeting techniques disclosed herein can keep the therapeutic construct from causing adverse events due to integration in or near a critical gene in the animal genome that would compromise its health and economic value.

In another embodiment, a vector, e.g., a Sleeping Beauty transposon carries a gene that can direct the demise of a cell in which either the therapeutic gene or the transposase gene is expressed (see FIGS. 3 and 4). Such a gene is colloquially referred to as a "suicide gene (SG)." The SG is expressed whenever the transgene is expressed. Such genes can be used to treat cancer. The HSV-TK gene has been used for this purpose (Borelli et al., 1988) and has been proposed for gene therapy as a killing agent for cancer cells (e.g., Anderson, 1998).

In another embodiment, a vector, e.g., a plasmid, comprises a Sleeping Beauty transposon that carries a gene that can be used for functional genomics to deliver to specific-genes or genetic loci a variety transposon trap vectors that lead to the elucidation of the function of a particular gene or chromosomal region. FIG. 4 shows a panoply of trap vectors that are used with Sleeping Beauty transposons in an unguided manner (Hackett et al., 2004; Wadman et al. 2005). Specific targeting of a carrier comprising a transposon to particular genes in the genomes of model organisms such as mice, rats, chickens, and fish allows the construction of specific lines of animals for research and development of pharmaceutical products and their testing (see Hackett et al., 2004 and U.S. Patent Application Publication No. US2004/0077572, "Transposon System and Methods of Use", Hackett et al.).

Referring to FIG. 4, transposons 402, 402', 402", including repeats 403, are indicated by brackets. The trap components comprise a reporter gene 404 (e.g., GFP) and splice acceptor (SA) 406, splice donor (SD) 408, and full 410 or minimal promoters 410' preceding the reporter genes. The exons of a gene of interest are indicated by 412, 412', 412". The process by which the reporter gene in the trap is express is indicated by the black lines 414, 416, 418, 420 under the reporter gene, depending on the type of trap, that is indicated on the right of each construct and include wild-type 422, gene-trap 424, 3-poly(A) trap 426, and enhancer-trap 428. pA 422 is a polyadenylation site. Gene traps, enhancer traps, and poly(A) traps are used in functional genomics studies to identify the functions of genes, the identification of transcriptional enhancers and polyadenylation/transcriptional termination sites, respectively. This information is of use in identifying genes that may be important therapeutic targets of new drugs.

Embodiments of a vector can comprise a transposon that includes a border element or an insulator sequence. Such a transposon may further comprise an exogenous DNA sequence. An exogenous sequence is a sequence that is intended to be introduced into an animal, a cell, a nucleus, or into another DNA sequence. A DNA-binding sequence may be natural or synthetic and may be naturally present in the animal that receives the exogenous sequence or it may be non-native to the animal. Examples of an exogenous sequence include, for example, a promoter, an enhancer, a marker sequence, a sequence encoding a therapeutic protein or a catalytic RNA, and insulator/border sequences, see U.S. patent application Ser. No. 10/758,237, filed Jan. 15, 2004, incorporated herein by reference. A transposon having an exogenous sequence may also contain an enhancer and a promoter and/or a combination of splicing acceptor and donor sites as well as polyadenylation and transcription termination signals. Embodiments of vectors also can comprise a transposon having an exogenous gene that encodes a suicide gene or other sequence that causes the demise of a cell or a cluster of cells, as described below. The suicide gene may also be used in combination with the border element/insulator sequence. The embodiments can be used in combination with both viral (e.g. lentiviruses, see U.S. Pat. No. 6,013,516) and non-viral vectors (e.g., transposons, see U.S. Pat. No. 6,489,458).

Additional Aspects of Applications of the Invention

Integration-site specific transgenic vectors, comprising transposons and viruses with or without targeting molecules, can be designed to overcome problems wherein randomly inserted genetic material may deleteriously affect expression of genes residing in chromosomes. Alternatively, such vectors can be used in functional genomics studies where the ability to localize their insertions often is important. The applications may be the same whether viral vectors or non-viral vectors such as Sleeping Beauty transposons are used. The following describes some of the applications to which site-specific integration can be applied.

A significant application is in human gene therapy, where adverse events due to unintended activation of genes have caused problems to patients. Site-specific integration of gene therapy vectors using targeting molecules can avoid inducement of inappropriate expression of chromosomal genes outside the vector itself. Integration-specific embodiments of gene therapy vectors, e.g., FIGS. 2B, 2C, 3B, and 3C will allow clinicians and their patients greater security that severe adverse consequences from the gene therapy will not occur.

Transgenic animals are used as bioreactors for the manufacture of biological reagents, proteins, of medical value (Jaenisch, 1988; Dove, 2000). Transgene expressed from vectors similar to those used for human gene therapy direct the synthesis of the commercially valuable proteins. Just as the health of humans is important, so also the health of the animal bioreactors (cow, sheep, goat, pig, fish) is important. The Integration Site-Specific vectors can be used for transgenesis of animals that result in reliable transgene expression without collateral damage to the animal because the embodiments designed herein work in all vertebrate animals (Hackett and Alvarez, 2000) with appropriate adjustment for the specific sequences or other species specific features.

The ability to target disruption of genes is extremely useful. It can be applied to gene therapy to destroy a gene that has been inappropriately activated or in bioreactors to eliminate a control mechanism that interferes with a desired phenotype. It also can be used to identify cancer genes (e.g., Collier et al., 2005; Dupuy et al., 2005).

Transgenic fish have been developed as a commercial food (Niiler, 2000). There are concerns of the effects of these fish, not only in terms of their augmented traits, but also in terms of unintended consequences of genetic engineering (Reichardt, 2000; Muir and Howard, 2002). Integration-specific vectors can be used for transgenesis of animals that result in reliable transgene expression without collateral damage to the animal because the embodiments designed for humans work in all vertebrate animals. Targeted integration may also facilitate approval by FDA and/or other governmental regulatory agencies.

Transgenic animals are extensively used for research applications. Functional genomics, the area of genomic science that seeks to attribute function to newly found genes from genome projects, depends on inactivation of genes as well as overexpression of genes. Integration-specific vectors can be used for transgenesis of animals that will result in reliable transgene expression without effects on other endogenous genes that would obscure the functional significance of the transgene in a model vertebrate animal.

Transgenesis is used in tissue culture to investigate the effects of transgenes. Implicit in the analyses is the assumption that the observed effects are due to the transgene and its intended activity (e.g., Hackett et al. 1999). Integration-specific transgenic vectors will give greater confidence in this fundamental assumption. Constructs for human gene therapy are first conducted in cultured cells and then in animals (e.g., Yant et al. 2000, Montini et al. 2002, Ohlfest et al., 2004, 2005a, Ohlfest 2005b).

Vectors

Nucleic acids can be incorporated into vectors. Vectors most often contain one or more expression cassettes that comprise one or more expression control sequences, wherein an expression control sequence is a DNA sequence that controls and regulates the transcription and/or translation of another DNA sequence or mRNA, respectively. Expression control sequences include, for example, promoter sequences, transcriptional enhancer elements, start codons, stop codons, and any other nucleic acid elements required for RNA polymerase binding, initiation, or termination of transcription. A wide range of expression control sequences is well known in the art and is commercially available. With respect to expression control sequences, the term 'operably linked' means that the expression control sequence and the inserted nucleic acid sequence of interest (also referred to herein as the exogenous nucleic acid sequence that is intended to be expressed, also referred to as the exogenous nucleic acid sequence) are positioned such that the inserted sequence is transcribed (e.g., when the vector is introduced into a host cell). A transcriptional unit in a vector may thus comprise an expression control sequence operably linked to an exogenous nucleic acid sequence. For example, a DNA sequence is operably linked to an expression-control sequence, such as a promoter when the expression control sequence controls and regulates the transcription and translation of that DNA sequence. The term "operably linked" includes having an appropriate start signal (e.g., ATG) in front of the DNA sequence to be expressed for translation and maintaining the correct reading frame to permit expression of the DNA sequence under the control of the expression control sequence to yield production of the desired protein product. Examples of vectors include: plasmids (which may also be a carrier of another type of vector), adenovirus, adeno-associated virus (AAV), lentivirus (e.g., modified HIV-1, SIV or FIV), retrovirus (e.g., ASV, ALV or MoMLV), and transposons (e.g., Sleeping Beauty, P-elements, Tol-2, Frog Prince, piggyBac).

There are a variety of promoters that could be used including, e.g., constitutive promoters, tissue-specific promoters, and inducible promoters. Promoters are regulatory signals that bind RNA polymerase in a cell to initiate transcription of a downstream (3'-direction) coding sequence.

Many different types of vectors are known. For example, plasmids and viral vectors, e.g., retroviral vectors, are known. Mammalian expression plasmids typically have an origin of replication, a suitable promoter and optional enhancer, and also any necessary ribosome binding sites, a polyadenylation site, splice donor and acceptor sites, transcriptional termination sequences, and 5' flanking non-transcribed sequences. In addition, the expression vectors preferably contain a gene to provide a phenotypic trait for selection of transformed host cells such as neomycin resistance for eukaryotic cell culture, or tetracycline or ampicillin resistance in *E. coli*. Retroviral vectors, which typically transduce only dividing cells, can be used. Adenoviral vectors, capable of delivering DNA to quiescent cells can be used. Another viral vector system with potential advantages is an adeno-associated viral vector.

Administration

One aspect of employing a non-viral vector, e.g., a transposon system, is the mechanism for its delivery (Hackett et al., 2005). One common method for transposons is the hydrodynamic delivery wherein a relatively large volume of transgenic DNA is injected into the circulatory system (the tail vein in mice) under high pressure—most of this DNA winds up in cells of the liver. Another method is to use negatively charged liposomes containing galactocerebroside, or complexed with polyethyleneimine (PEI), which may be complexed with ligands such as lactose or galactose for tissue-specific uptake and which have been effective in delivering nucleic acids into hepatoma cells, primary hepatocytes and liver and lung cells in living mice.

The delivery of transposons, in plasmid carrier molecules, to any tissue in the body is contemplated, including cells found in blood, liver, lung, pancreas, muscle, eye, brain, nervous system, organs, dermis, epidermis, cardiac, and vasculature. For example delivery may be by, direct injection into or near the desired tissue, complexation with molecules that preferentially or specifically bind to a target in the desired tissue, control release, oral, intramuscular, and other delivery systems that are known to those skilled in these arts. Another embodiment for delivery is electroporation, e.g., electroporation of cells in the blood using an electroporator. Cells may be microinjected or electroporated in vitro or in vivo; detailed materials and methods for such processes are provided in U.S. patent Ser. No. 10/758,237, filed Jan. 15, 2004, entitled "Materials and Methods of Using Transposons Encoding RNAi", which is incorporated by reference herein in its entirety. RNAi is described in greater detail elsewhere (Yin and Wan, 2002; Scherer and Rossi, 2003) and below. As categorized by Yin and Wan, RNAi includes long double stranded RNAs, long single stranded sense RNA, single stranded RNAs that form duplexes, short double stranded RNAs, and short antisense RNAs. RNAi is the subject of U.S. patent and PCT applications, e.g., certain of the following: US20030125281; US20030130186; US20030124513; US20030119017; US20030144239; US20030166282; US20030148519; US20030157691; US20030153519; US20030139363; US20030166512; US20030036056; WO03056022; WO03020931; WO03008573; WO0244321; WO03070895; WO03070193; WO03070750; WO03070918; WO03070914; WO03066650; WO03068797; WO02097114; WO9946372; WO0060115; W09519788; WO09206988; and U.S. Pat. Nos. 6,562,570 5,985,661. 5,750,380 5,750,380 5,272,262 5,149,796; 5,144,019; and 5,110,802. Use of RNAi and shRNA and other materials and methods as described in these publications is contemplated in combinations with the embodiments described elsewhere herein.

Examples of delivery of certain embodiments herein include via injection, such as intravenously, intramuscularly, or subcutaneously, and in a pharmaceutically acceptable carriers, e.g., in solution and sterile vehicles, such as physiological buffers (e.g., saline solution or glucose serum). The embodiments may also be administered orally or rectally, when they are combined with pharmaceutically acceptable solid or liquid excipients. Embodiments can also be administered externally, for example, in the form of an aerosol with a suitable vehicle suitable for this mode of administration, for example, nasally. Further, delivery through a catheter or other surgical tubing is possible. Alternative routes include tablets, capsules, and the like, nebulizers for liquid formulations, and inhalers for lyophilized or aerosolized agents.

Presently known methods for delivering molecules in vivo and in vitro, especially small molecules, nucleic acids or polypeptides, may be used for the embodiments. Such methods include microspheres, liposomes, other microparticle vehicles or controlled release formulations placed in certain tissues, including blood. Examples of controlled release carriers include semi-permeable polymer matrices in the form of shaped articles, e.g., suppositories, or microcapsules and U.S. Pat. Nos. 5,626,877; 5,891,108; 5,972,027; 6,041,252; 6,071,305, 6,074,673; 6,083,996; 6,086,582; 6,086,912; 6,110,498; 6,126,919; 6,132,765; 6,136,295; 6,142,939; 6,235,312; 6,235,313; 6,245,349; 6,251,079; 6,283,947; 6,283,949; 6,287,792; 6,296,621; 6,309,370; 6,309,375; 6,309,380; 6,309,410; 6,317,629; 6,346,272; 6,350,780; 6,379,382; 6,387,124; 6,387,397 and 6,296,832. Moreover, formulations for administration can include, for example, transdermal patches, ointments, lotions, creams, gels, drops, suppositories, sprays, liquids, and powders.

Electroporation is a technology that has been used in research laboratories throughout the world for the past 20 years. The primary application has been in transfection of eukaryotic and prokaryotic cells. The process subjects cells to a pulsed electric field for a short duration, resulting in permeabilization of the lipid bilayer of the cell membrane. This permeability develops in microseconds and resolves in seconds to minutes. While a physical "pore" has been observed under some circumstances, in most situations the permeability change is probably related to transient reorientation of membrane phospholipids. During the permeable period, both polar and non-polar molecules of various sizes can diffuse through the permeable areas according to concentration gradients. In addition, the electric field provides a force by which charged particles move into the cell ("electrophoretic-"mechanism). Various molecules can be inserted into cells, including drugs, DNA, proteins, or other biomolecules.

Cells that may be exposed to, or transfected by, transposons can be obtained from a variety of sources including bacteria, fungi, plants and animals, e.g., a vertebrate or an invertebrate; for example, crustaceans, mollusks, fish, birds, mammals, rodents, ungulates, sheep, swine and humans. Cells that may be exposed to a transposon include, e.g., lymphocytes, hepatocytes, neural cells, muscle cells, a variety of blood cells, stem cells for various tissues and organs and a variety of cells of an organism. These cells include stem cells such as CD34+ hematopoietic stem cells, as well as tissue-specific cell types such as hepatocytes and sinusoidal epithelial cells in liver and type-2 pneumocytes in the lung.

Nucleic Acids

As used herein, the term nucleic acid refers to both RNA and DNA, including, for example, cDNA, genomic DNA, synthetic (e.g., chemically synthesized) DNA, as well as naturally occurring and chemically modified nucleic acids, e.g., synthetic bases or alternative backbones. A nucleic acid molecule can be double-stranded or single-stranded (i.e., a sense or an antisense single strand). An isolated nucleic acid refers to a nucleic acid that is separated from other nucleic acid bases that are present in a genome, including nucleic acids that normally flank one or both sides of a nucleic acid sequence in a vertebrate genome (e.g., nucleic acids that flank a gene). The term isolated as used herein with respect to nucleic acids also includes non-naturally-occurring nucleic acid sequences, since such non-naturally-occurring sequences are not found in nature and do not have immediately contiguous sequences in a naturally occurring genome.

An isolated nucleic acid can be, for example, a DNA molecule, provided at least one of the nucleic acid sequences normally found flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences as well as DNA that is incorporated into a vector, an autonomously replicating plasmid, a virus (e.g., a retrovirus, lentivirus, adenovirus, adeno-associated virus, or herpes virus), or into the genomic DNA of a prokaryote or eukaryote. In addition, an isolated nucleic acid can include an engineered nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not considered an isolated nucleic acid because such sources do not indicate a role for the nucleic acid or its uses. Indeed, there is often no knowledge of the sequences present in such sources until their presence is hypothesized as a result of using hindsight in light of a new sequence.

EXAMPLES

Functional Genomics

Example 1

Site-specific Integration in Cultured Human Cells

In human HeLa cells, site-specific integration of a Sleeping Beauty transposon that confers neo resistance will be tested (Scheme 1). Referring to Scheme 1, a 250-basepair segment of DNA corresponding to exon4 of pitx2 will be amplified, denatured, and coated with RecA protein. Cells will be transfected with the pT2/mCaggs-neo Sleeping Beauty transposon, pCMV-SB11, and RecA-coated pitx2 filaments. Cells will be selected with G418 for 12 days in culture. DNA will be isolated and site-specific activity will be assessed by PCR amplification by PCR. Once site-specific integration is observed, the experiment will be repeated and individual G418 clones will be isolated to determine the frequency that site-specific Sleeping Beauty integration has occurred. The ability of RecA-coated filaments to promote preferred sites of integration for Sleeping Beauty will be measured by looking for integration events near the pitx2 gene.

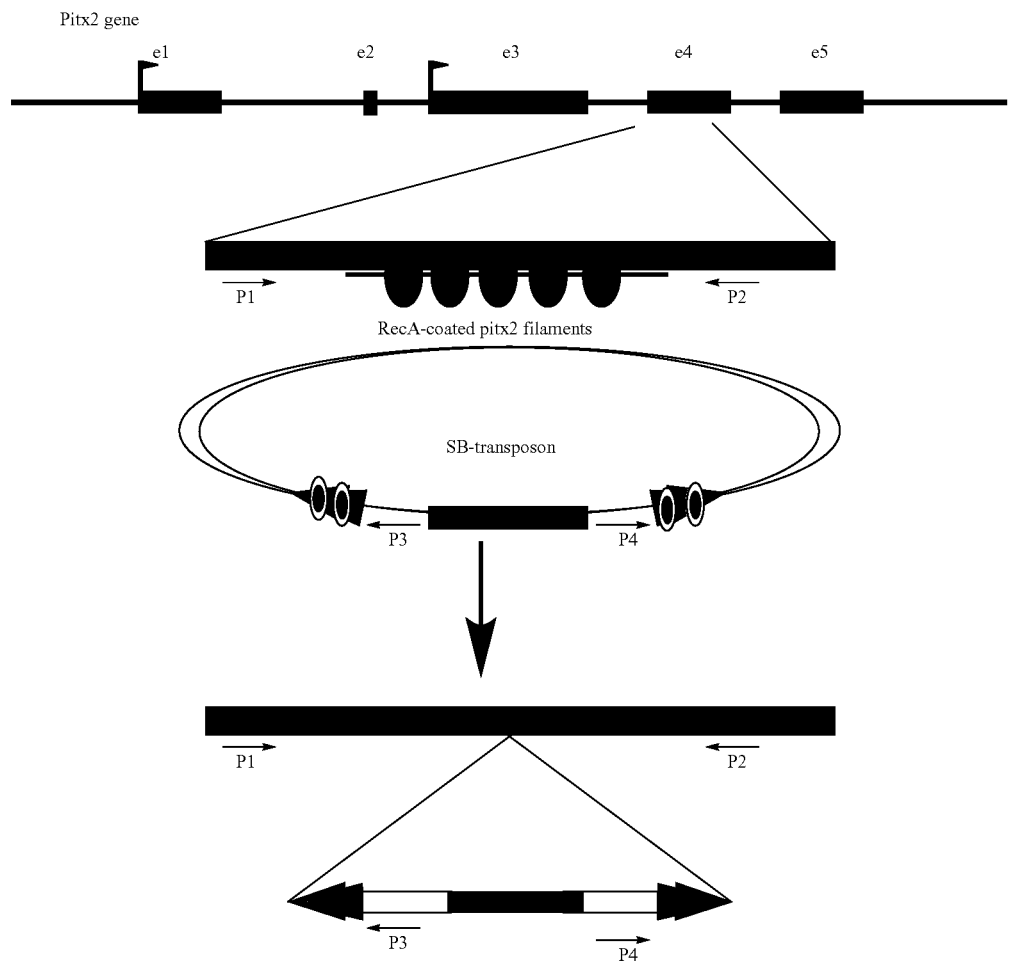

Example 2

RecA-mediated Site-specific Integration

A similar approach to Example 1 will be tested in zebrafish to assess the ability of RecA-coated filaments to promote site-specific integration of Sleeping Beauty transposons. For this, RecA-coated pitx2 filaments will be injected into the 1- to 2-cell zebrafish embryo with SB11 RNA and a Sleeping Beauty transposon that expresses the green fluorescent protein (GFP) from an EF-1α promoter. Following injection, embryos that are expressing GFP will be harvested at 24 hours post-fertilization for DNA isolation. DNA will be analyzed for site-specific activity by PCR amplification using the same approach as above. Once site-specific integration activity is observed in early embryos, similar injected embryos will be raised to adulthood and their progeny will be analyzed to determine the frequency of site-specific integration of Sleeping Beauty transposons.

Example 3

Molecular Tethering of Carrier Molecules to RecA-Deformed DNA for Site-specific Targeting of Integration The ability of RecA-gal4 and Rad51-gal4 coated pitx2 filaments will be tested for their ability to promote site-specific integration of Sleeping Beauty transposons by tethering the Sleeping Beauty transposon to specific regions in HeLa cells. For this, both N-terminal and C-terminal fusion proteins of gal4 to RecA and Rad51 will be produced. A 250-bp piece of pitx2 DNA from exon 4 will be coated with these fusion proteins either with or with out native RecA or Rad51. These filaments will be transfected into cells with pCMV-SB11 and pT2/mCaggs-neo/UAS. pT2/mCaggs-neo/UAS has UAS sites that are specific for gal4 in the vector backbone next to the antibiotic resistance gene. Cells will be selected with G418 for 12 days in culture. DNA will be isolated, and site-specific activity will be assessed by PCR amplification with 4 primer sets as above. Once site-specific integration is observed, the experiment will be repeated and individual G418 clones will be isolated to determine the frequency that site-specific Sleeping Beauty integration has occurred.

Example 4

Morphilino-induced DNA Deformation of DNA for Targeted Integration

Morpholinos will also be tested to promote site-specific integration of Sleeping Beauty transposons in zebrafish. Morpholinos, because of their strong binding affinity for DNA, which is greater than native DNA-to-DNA hybridization, may bind to double-stranded DNA at a target site. The strand of native DNA that is displaced by the morpholino will then be available for interaction with a transposase so that a transposon may be introduced at the site of the target DNA. Similar to the approach above with RecA-coated filaments, a morpholino against the fourth exon of pitx2 will be injected into the 1- to 2-cell zebrafish embryo with SB11 RNA and a Sleeping Beauty transposon that expresses GFP from an EF-1α promoter. Following injection, embryos that are expressing GFP will be harvested at 24 hours post-fertilization for DNA isolation. DNA will be analyzed for site-specific activity by PCR amplification. Once site-specific integration activity is observed in early embryos, similar injected embryos will be raised to adulthood and their progeny will be analyzed to determine the frequency of site-specific integration of Sleeping Beauty transposons. In some embodiments, a morpholino is the target-binding moiety to which the molecular tether binds.

Example 5

Site-specific Integration in the Genome of a Model Species for Functional Genomics The ability of RecA-gal4 and Rad51-gal4 coated pitx2 filaments also will be tested for their ability to promote site-specific integration of Sleeping Beauty transposons by tethering the Sleeping Beauty transposon to specific regions in zebrafish embryos. Similar to the above strategy, both N-terminal and C-terminal fusion proteins of gal4 to RecA and Rad51 will be tested. A 250-bp sequence of pitx2 DNA from exon 4 will be coated with these fusion proteins either with or with out native RecA or Rad51. The pitx2 filaments will be injected into the 1 to 2-cell zebrafish embryo with SB11 RNA and a Sleeping Beauty transposon that expresses the green fluorescent protein (GFP) from an EF-1α promoter. Following injection, embryos that are expressing GFP will be harvested at 24 hours post-fertilization for DNA isolation. DNA will be analyzed for site-specific activity by PCR amplification using the same approach as above. Once site-specific integration activity is observed in early embryos, similar injected embryos will be raised to adulthood and their progeny will be analyzed to determine the frequency of site-specific integration of Sleeping Beauty transposons.

Example 6

Site-specific Delivery of a Therapeutic Transposon to Human Hematopoietic Stem Cells. Method to Deliver to a Single Site The goal is to deliver a therapeutic gene to a single site in the genome. The selected site is a ribosomal protein L32 pseudogene that lacks introns (Lander et al., 2001). The targeted area spans an intron so that the site-specific binding is to the end of exon-1 and the beginning of exon-2. The carrier plasmid contains a lexA-binding domain as shown in FIG. 3C. A DNA molecular tether (Tether/LexL32) containing a lexA-binding site and a binding site for the L32 pseudogene is coinjected at a 100:1 ratio of with the plasmid pKT2/PGK-FancC that has a Sleeping Beauty transposon with a FancC gene under the direction of the PGK promoter that directs transcription of the gene that encodes phosphoglycerol kinase. Sleeping Beauty transposase can be provided either by an mRNA or a plasmid with the Sleeping Beauty transposase under the direction of a Ubiquitin promoter. Bone marrow cells that have a mutation in the Fanconi Anemia Type C gene are collected by standard clinical procedures and electroporated under sterile, clinical conditions with the pKT2/PGK-FancC Sleeping Beauty transposon, transposase source and Tether/LexL32. $CD34^+$ cells will be isolated from the bone marrow sample by column filtration using standard clinical procedures. Following electroporation, cells are re-engrafted into the patient who is followed. Success will be monitored by amelioration of the anemia with cells that are "marked" by the transposon similar to what is done with retroviral gene therapy (Kustikova et al., 2005). Marked cells can be analyzed by PCR gene to determine integration specificity in and around (within 10 kbp) of the L32 pseudogene.

Example 7

Site-specific Delivery of a Therapeutic Transposon to Human Hematopoietic Stem Cells. Method to Deliver to a Family of Sites The goal is to deliver a therapeutic gene to any of a number of sites in the human genome. About 13,000 copies of the ca. 350-bp repetitive element Zaphod are spread throughout the human genome (Lander et al., 2001). They belong to the hAT family of repetitive elements, which is not related to the Tc1/mariner family of transposons to which the Sleeping Beauty transposon belongs. Thus, the selected site is likely to be hit by the integrating transposons and used instead of other random sites. As in Example 6, the carrier plasmid contains a lexA-binding domain as shown in FIG. 3C. A DNA molecular tether (Tether/LexZaphod)-containing a lexA-binding site and a binding site for the Zaphod repetitive element is coinjected at a 100:1 ratio of with the plasmid pKT2/PKG-FancC that has a Sleeping Beauty transposon with a FancC gene under the direction of a PGK promoter. Sleeping Beauty transposase can be provided either by an mRNA or a plasmid with the Sleeping Beauty transposase under the direction of a Ubiquitin promoter. The procedure and analysis are similar to those in Example 6.

REFERENCES

The patents, patent applications, journal articles, and publications set forth in this application are hereby incorporated by reference herein to the extent that they are not contrary to the explicit disclosure herein.

Anderson, W. F. (19998). Human gene therapy. Nature 392 (suppl): 25-30.

Ausubel, et al. (1994). *Current Protocols in Molecular Biology*, Contents V. 1, 2, and 3. Table of Contents.

Bae, K-H. et al. and J-S. Kim (2003). Human zinc fingers as building blocks in the construction of artificial transcription factors. Nature Biotech 21: 275-280.

Basye J., Trent, J. O., Gao, D. and Ebbinghaus, S. (2001). Triplex formation by morpholino oligodeoxyribonucleotides in the HER-2/neu promoter requires the pyrimidine motif. Nucleic Acids Research 29: 4873-4880.

Beerli, R. R., B. Dreier, and C. F. Barbas III (2000). Positive and negative regulation of endogenous genes by designed transcription factors. Proc. Natl. Acad. Sci. USA 97: 1495-1500.

Bibikova, M., K. Beumer, J. K. Trautman and D. Carroll (2003). Enhancing gene targeting with designed zinc finger nucleases. Science 300: 764.

Borrelli, E., Heyman, R., Hsi, M. and Evans, R. M. (1988). Targeting of an inducible toxic phenotype in animal cells. Proceedings of the National Academy of Sciences USA 85: 7572-7576.

Bushman, F. D. (2002). Integration site selection by lentiviruses: biology and possible control. Current Topics in Microbiology and Immunology 261: 165-177.

Check, E. (2003). Harmful potential of viral vectors fuels doubts over gene therapy. Nature 423, 573-574.

Coates, C. J., Kaminski, J. M., Summers, J. B., Segal, D. J., Miller, A. D. and Kolb, A. F. (2005). Site-directed genome modification: derivatives of DNA-modifying enzymes as targeting tools. Trends Biotech. 23: 407-419.

Collier, L. S., Carlson, C. M., Ravimohan, S., Dupuy, A. J. and Largaespada, D. A. (2005), Cancer gene discovery in solid tumours using transposon-based somatic mutagenesis in the mouse. Nature 436: 272-276.

Cui, Z., Y. Yang, C. D. Kaufman, D. Agalliu and P. B. Hackett (2003). RecA-mediated, targeted mutagenesis in zebrafish. Mar. Biotech. 5: 174-184.

Desjarlais, J. R., and Berg, J. M. (1992). Toward rules relating zinc finger protein sequences and DNA binding site preferences. Proceedings of the National Academy of Sciences USA 89: 7345-7349.

Ding, S., Wu, X., Li, G., Han, M., Zhuang, Y., and Xu, T. (2005). Efficient transposition of the piggyBac (PB) transposon in cells and mice. Cell (in press).

Dove, A. (2000). Milking the genome for profit. Nature Biotech. 18: 1045-1048.

Dupuy, A. J., Fritz, S., and Largaespada, D. A. (2001). Transposition and gene disruption using a mutagenic transposon vector in the male germline of the mouse. Genesis 30: 82-88.

Dupuy, A. J., Clark, K., Carlson, C. M., Fritz, S., Davidson, A. E., Markley, K. M., Finley, K., Fletcher, C. F., Ekker, S. C., Hackett, P. B., et al. (2002). Mammalian germ-line transgenesis by transposition. Proceedings of the National Academy of Sciences USA 99: 4495-4499.

Dupuy, A. J., Akagi, K., Largaespada, D. A., Copeland, N. G. and Jenkins, N. A. (2005). Mammalian mutagenesis using a highly mobile somatic Sleeping Beauty transposon system. Nature 436: 221-226.

Engelman, A. (2005). The ups and downs of gene expression and retroviral integration. Proceedings of the National Academy of Sciences USA 102: 1275-1276.

Essner, J. J., McIvor R. S. and Hackett, P. B. (2005). Awakening of gene therapy with Sleeping Beauty transposons. Current Opinion in Pharmacology 5(5): (in press).

Evans, R. M. and Hollenberg, S. M. (1988). Zinc fingers: gilt by association. Cell 52: 1-3.

Fischer, S. E., Wienholds, E., and Plasterk, R. H. (2001). Regulated transposition of a fish transposon in the mouse germ line. Proceedings of the National Academy of Sciences USA 98: 6759-6764.

Fletcher, G. L., Shears, M. A., Yaskowiak, E. S., King, M. J. and Goddard, S. V. (2004). Gene transfer: potential to enhance the genome of Atlantic salmon for aquaculture. Australian Journal of Experimental Agriculture 44: 1095-1100.

Glover, D. J., Lipps, H. J. and Jans, D. A. (2005). Towards safe, non-viral therapeutic gene expression in humans. Nature Reviews Genetics 6: 299-310.

Groth, A. C., Olivares, E. C., Thyagarajan, B. and Calos, M. P. (2000). A phage integrase directs efficient site-specific integration in human cells. Proceedings of the National Academy of Sciences USA 97: 5995-6000.

Groth, A. C. and Calos, M. P. (2004). Phage integrases: biology and applications. Journal of Molecular Biology 335: 667-678.

Hacein-Bey-Abina, S., von Kalle, C., Schmidt, M., Le Deist, F., Wulffraat, N., McIntyre, E., Radford, I., Villeval, J. L., Fraser, C. C., Cavazzana-Calvo, M., and Fischer, A. (2003). A serious adverse event after successful gene therapy for X-linked severe combined immunodeficiency. New England Journal of Medicine 348, 255-256.

Hackett, P. B., Izsvak, Z., Ivics, Z. and Caldovic, L. (1999). Development of genetic tools for transgenic animals. IN Transgenic Animals in Agriculture. CAB International, Wallingford, UK. 19-35.

Hackett, P. B. and Alvarez, M. C. (2000). The molecular genetics of transgenic fish. Recent Advances in Marine Biotechnology 4: 77-145.

Hackett, P. B., Clark, K. J., Ekker, S. E. and Essner, J. J. (2004). Applications of transposable elements in fish for transgenesis and functional genomics. *Fish Development and Genetics* (Z. Gong and V. Korzh, eds.) Chapter 16, 532-580.

Hackett, P. B., Ekker, S. C., Largaespada, D. A. and McIvor R. S. (2005). Sleeping Beauty transposon-mediated gene therapy for prolonged expression. Advances in Genetics 54: 187-229.

Han, J. S. and Boeke, J. D. (2004). A highly active synthetic mammalian retrotransposon. Nature 429: 314-318.

Hardison, R. C., Sawada, I., Cheng, J. F., Shen, C. K. and Schmid, C. W. (1986). A previously undetected pseudogene in the human alpha globin gene cluster. Nucleic Acids Research 14: 1903-1911.

Holman, A. G. and Coffin, J. M. (2005). Symmetrical base preferences surrounding HIV-1, avian sarcoma/leucosis virus, and murine leukemia virus integration sites. Proceedings of the National Academy of Sciences USA 102: 6103-6107.

Horie, K., Kuroiwa, A., Ikawa, M., Okabe, M., Kondoh, G., Matsuda, Y., and Takeda, J. (2001). Efficient chromosomal transposition of a Tc1/mariner-like transposon Sleeping Beauty in mice. Proceedings of the National Academy of Sciences USA 98: 9191-9196.

Horie, K., Yusa, K., Yae, K., Odajima, J., Fischer, S. E., Keng, V. W., Hayakawa, T., Mizuno, S., Kondoh, G., Ijiri, T., et al. (2003). Characterization of Sleeping Beauty transposition and its application to genetic screening in mice. Molecular and Cellular Biology 23: 9189-9207.

Igoucheva, O., Alexeev, V. and Yoon, K. (2004). Oligonucleotide-directed mutagenesis and targeted gene correction. A mechanistic point of view. Current Molecular Medicine 4: 445-463.

Ivics, Z., Hackett, P. B., Plasterk, R. H. and Izsvak, Z. (1997). Molecular reconstruction of Sleeping Beauty, a Tc1-like transposon from fish, and its transposition in human cells. Cell 91: 501-510.

Jaenisch, R. (1988). Transgenic animals. Science 240: 1468-1474.

Kaminski, J. M., Huber, M. R., Summers, J. B. and Ward, M. B. (2002). Design of a non-viral vector for site-selective, efficient integration into the human genome. FASEB 16: 1242-1247.

Kaminski, J. M., Vally, M., Teneholz, T., Summers, J. B. and Coates, C. J. (2005). Site-specific transposon integration. Molecular Therapy 11: S424.

Koga, A., Iida, A., Kamiya, M., Hayashi, R., Hori, H., Ishikawa, Y., and Tachibana, A. (2003). The medaka fish Tol2 transposable element can undergo excision in human and mouse cells. Journal of Human Genetics 48: 231-235.

Kolb, A. F., Coates, C. J., Kaminski, J. M., Summers, J. B., Miller, A. D. and Segal D. J. (2005). Site-directed genome modification: nucleic acid and protein modules for targeted integration and gene correction. Trends Biotech. 23: 399-406.

Kustikova, O., Fehse, B., Modlich, U., Yang, M., Dullmann, J., Kamino, K., von Neuhoff, N., Schlegelberger, B., Li, Z. and Baum, C. (2005). Clonal dominance of hematopoietic stem cells triggered by retroviral gene marking. Science 308: 1171-1174.

Lander, E. S. et al. (2001). Initial sequencing and analysis of the human genome. Nature 409: 860-921.

Linden, R. M. (2002). Gene therapy gets the Beauty treatment. Nature Biotechnology 20: 987-988.

Liu, G., Geurts, A. M., Yae, K. Srinivassan, A. R., Fahrenkrug, S. C., Largaespada, D. A., Olson, W. K., Takeda, J., Horie, K. and Hackett, P. B. (2005). Target-site preference for Sleeping Beauty transposons. Journal of Molecular Biology 346:161-173.

Marshall E. (2002). Clinical research. Gene therapy a suspect in leukemia-like disease. Science. 298: 34-35.

Maxfield, L. F., Fraize, C. D. and Coffin, J. M. (2005). Relationship between retroviral DNA-integration-site selection and host cell transcription. Proceedings of the National Academy of Sciences USA 102: 1436-1441.

Miskey, C., Izsvak, Z., Plasterk, R. H. A., and Ivics, Z. (2003). The Frog Prince: a reconstructed transposon from Rana pipiens with high transpositional activity in vertebrate cells. Nucleic Acids Research 31: 6873-6881.

Mitchell, R. S., Beitzel, B. F., Schroder, A. R., Shinn, P., Chen, H., Berry, C. C., Ecker, J. R. and Bushman, F. D. (2004). Retroviral DNA integration: ASLV, HIV, and MLV show distinct target site preferences. Public Library of Science 2: 1127-1136.

Mok, H. P. and Lever, A. M. (2005). Vector integration: location, location, location. Gene Therapy 12: 1-2.

Montini, E., Held, P. K. Noll, M., Morcinek, N., Al-Dhalimy, M., Finegold, M., Yant, S., Kay, M. A. and Grompe, M. (2002). In vivo correction of murine tyrosinemia type I by DNA-mediated transposition. Molecular Therapy 6: 759-769.

Muir, W. M. and Howard, R. D. (2002). Assessment of possible ecological risks and hazards of transgenic fish with implications for other sexually reproducing organisms. Transgenic Research 11: 101-114.

Nakai, H., Montini, E., Fuess, S., Storm, T. A., Grompe, M. and Kay, M. A. (2003). AAV serotype 2 vectors preferentially integrate into active genes in mice. Nature Genetics 34: 297-302.

Niiler, E. (2000). FDA, researchers consider first transgenic fish. Nature Biotechnology 18: 143.

Ohlfest, J. R., Lobitz, P. D., Perkinson, S., G., and Largaespada, D. A. (2004). Integration and long-term expression in xenografted human glioblastoma cells using a plasmid-based transposon system. Molecular Therapy 10: 260-268.

Ohlfest, J. R., J. L. Frandsen, S. Fritz, P. D. Lobitz, S. G. Perkinson, K. J. Clark, N. S. Key, R. S. McIvor, P. B. Hackett and D. A. Largaespada (2005a). Phenotypic correction and long-term Factor VIII expression in hemophilic mice by immunotolerization and nonviral gene transfer using the Sleeping Beauty transposon system. Blood 105: 2691-2698

Ohlfest, J. R., Z. L. Demorest, Y. Motooka, I. Vengco, S. Oh, E. Chen, F. A. Scappaticci, R. J. Saplis, S. C. Ekker, W. C. Low, A. B. Freese, and D. A. Largaespada (2005b). Combinatorial anti-angiogenic gene therapy by nonviral gene transfer using the Sleeping Beauty transposon causes tumor regression and improves survival in mice bearing intracranial human glioblastoma. Molecular Therapy 12: (in press)

Olivares, E. C., Hollis, R. P., Chalberg, T. W., Meuse, L., Kay, M. A. and Calos, M. P. (2002). Site-specific genomic integration produces therapeutic Factor IX levels in mice. Nature Biotechnology 20: 1124-1128.

Pabo, C. O. and Sauer, R. T. (1992). Transcription factors: structural families and principles of DNA recognition. Ann. Rev. Biochem. 61: 1053-1095.

Pomerantz, J. L., P. A. Sharp, and C. O. Pabo (1995). Structure-based design of transcription factors. Science 267: 93-96.

Ptashne, M. (1988). How eukaryotic transcriptional activators work. Nature 335: 683-689.

Rao, J. E., Miller, P. S. and Craig, N. L. (2000). Recognition of triple-helical DNA structures by transposon Tn7. Proceedings of the National Academy of Sciences USA 97: 3936-3941.

Reichardt, T. (2000). Will souped up salmon sink or swim? Nature 406: 10-12.

Sanchez-Garcia, I. and T. H. Rabbitts (1994). The LIM domain: a new structural motif found in zinc-finger-like proteins. Trends Genet. 10: 315-320.

Scherer, L. J. and Rossi, J. J. (2003). Approaches for the sequence-specific knockdown of mRNA. Nature biotech. 21: 1457-1465.

Schleif, R. (1988). DNA binding by proteins. Science 241: 1182-1187.

Schroder, A. R. W., Shinn, P., Chen, H., Berry, C., Ecker, J. R. and Bushman, F. (2002). HIV-1 integration in the human genome favors active genes and local hotspots. Cell 110: 521-529.

Strayer, D. S., R. Akkina, B. A. Bunnell, B. Dropulic, V. Planelles, R. J. Pomerantz, J. J. Rossi and J. A. Zaia (2005). Current status of gene therapy strategies to treat HIV/AIDS. Mol. Therap. 11: 823-842.

Struhl, K. (1989). Helix-turn-helix, zinc-finger, and leucine-zipper motifs for eukaryotic transcriptional regulatory proteins. Trends in Biological Sciences 14: 137-140.

Thomas, C. E., Ehrhardt, A., and Kay, M. A. (2003). Progress and problems with the use of viral vectors for gene therapy. Nature Review of Genetics 4: 346-357.

Urnov, F. D., Miller, J. C., Lee, Y. L., Beausejour, C. M., Rock, J. M., Augustus, S., Jamieson, A. C., Porteus, M. H., Gregory, P. D. and Holmes, M. C. (2005). Highly efficient endogenous human gene correction using designed zinc-finger nucleases. Nature 435: 646-651.

Venter, J. C. et al. (2001). The sequence of the human genome. Science 291: 1304-1351.

Verma, I. (2002). Success and setback: another adverse event. Molecular Therapy 6: 565-566.

Verma, I. M. and Somia, N. (1997). Gene therapy—promises, problems and prospects. Nature 389: 239-242.

Vigdal, T. J., Kaufman, C. D., Izsvak, Z., Voytas, D. F. and Ivics Z (2002).

Common physical properties of DNA affecting target site selection of Sleeping Beauty and other Tc1/mariner transposable elements. Journal of Molecular Biology 323: 441-452.

Wadman, S. A., Clark, K. J. and Hackett, P. B. (2005). Fishing for answers with transposons. Marine Biotechnology 7(3): 135-141.

Wall, R. J. (2001). Pronuclear Injection. Cloning Stem Cells 3: 209-220.

Williams, D. A., and Baum, C. (2003). Gene therapy—new challenges ahead. Science, 302: 400-401.

Wu, X. , Li, Y., Crise, B. and Burgess, S. M. (2003). Transcription start regions in human genome are favored targets for MLV integration. Science 300: 1749-1751.

Wu, X., Li, Y., Crise, B., Burgess, S. M., and Munroe, D. J. (2005). Weak palindromic consensus sequences are a common feature found at the integration target sites of many retroviruses. Journal of Virology 79: 5211-5214.

Yant, S. R., Meuse, L., Chio, W., Ivics, Z., Izsvak, Z. and Kay, M. A. (2000). Somatic integration and long-term transgene expression in normal and haemophilic mice using a DNA transposon system. Nature Genetics 25: 35-41.

Yant, S. R., Wu, X., Huang, Y., Garrison, B., Burgess, S. M. and Kay, M. A. (2005a). High-resolution genome-wide mapping of transposon integration in mammals. Molecular and Cellular Biology 25: 2085-2094.

Yant, S. R., Huang, Y. and Kay, M. A. (2005b). Fusion proteins consisting of the Sleeping Beauty transposase and the polydactyl zinc finger protein E2C direct transposition integration into a unique human chromosomal sequence. Molecular Therapy 11: S424.

Yin, J. Q. and Y. Wan (2002). RNA-mediated gene regulation system: now and the future. International Journal of Molecular Medicine 10: 355-365.

The invention claimed is:

1. An isolated molecular tether comprising a RecA or Rad51 protein, a carrier-binding domain and a spacer connecting the RecA or Rad51 protein to the carrier-binding domain, wherein the RecA or Rad51 protein is further bound to a single-stranded nucleic acid segment having a sequence for binding to a target DNA segment, and wherein the carrier-binding domain has specific binding affinity for a nucleic acid sequence, with the carrier-binding domain and the spacer being polypeptides.

2. The molecular tether of claim 1, wherein the carrier-binding domain comprises one or more zinc fingers, at least one helix-turn-helix motif, or at least one helix-loop-helix motif.

3. A purified vector system for targeting a double-stranded target-DNA segment, the system comprising a molecular tether and a carrier comprising a vector with an expressible nucleic acid segment, with the molecular tether comprising:
   a target-DNA-binding domain comprising a polypeptide that associates with a single-stranded DNA to thereby have a specific binding affinity for a target double-stranded DNA segment;
   a carrier-binding domain that is a polypeptide having a specific binding affinity for a DNA segment located on the carrier; and
   a spacer sequence that is a polypeptide covalently bonded to the target-DNA-binding domain and the carrier-binding domain.

4. The system of claim 3, wherein the carrier-binding domain or the target-DNA-binding domain comprises one or more zinc fingers.

5. The system of claim 3, wherein the target-DNA-binding domain or the carrier-binding domain comprises at least one helix-turn-helix motif or at least one helix-loop-helix motif.

6. The system of claim 3, wherein the target-DNA-binding domain or the carrier-binding domain comprises a triple helix-stabilizing protein.

7. The system of claim 6, wherein the triple-helix-stabilizing protein is a RecA protein or a Rad51 protein.

8. The system of claim 6, wherein the triple-helix-stabilizing protein is a RecA or Rad51, and the RecA or Rad51 is associated with an single-stranded nucleic acid segment having a sequence that is matched to the target double-stranded DNA segment's sequence.

9. The system of claim 3, wherein the carrier comprises a plasmid.

10. The system of claim 3, wherein the vector comprises a transposon.

11. The system of claim 10, wherein the vector comprises a Sleeping Beauty transposon.

12. An isolated molecular tether comprising:
   a target DNA-binding domain comprising a polypeptide that associates with a single-stranded DNA to thereby have a specific binding affinity for a target-DNA segment that is double-stranded;
   a carrier-binding domain that specifically binds to a DNA segment on a carrier; and
   a spacer covalently bonded to the target-DNA-binding domain and the carrier-binding domain
   with the spacer and the carrier-binding domains being polypeptides.

13. The molecular tether of claim 12, wherein the target DNA-binding domain or the carrier-binding domain comprises at least one helix-turn-helix motif or at least one helix-loop-helix motifs.

14. The molecular tether of claim 12, wherein the target-DNA-binding domain or the carrier-binding domain comprises one or more zinc fingers.

15. The molecular tether of claim 12, wherein the target-DNA-binding domain or the carrier-binding domain comprises a triple-helix-stabilizing protein.

16. The molecular tether of claim 15, wherein the triple-helix-stabilizing protein comprises a RecA protein or a Rad51 protein.

17. The system of claim 3, wherein the carrier comprises a viral vector-based genome comprising an expressible DNA segment.

18. A nucleic acid segment comprising an mRNA or a DNA encoding the molecular tether of claim 12.

19. A purified ex vivo vector system for targeting a double-stranded target-DNA segment in a patient that comprises a purified pharmaceutically acceptable preparation that comprises:
    a polypeptide molecular tether specifically bound to a carrier via protein-to-DNA specific binding, with
    the carrier comprising:
        a Sleeping Beauty transposon vector and a DNA segment for protein-to-DNA specific binding to the tether, and
    the molecular tether comprising:
        a RecA or Rad51 polypeptide associated with a single-stranded nucleic acid and having a specific binding affinity for a predetermined target double-stranded DNA segment in a chromosome of a patient;
        a polypeptide carrier-binding domain with either a helix-loop-helix motif, a helix-turn-helix motif, or at least one zinc finger motif, having a specific binding affinity for the DNA segment on the carrier; and
        a spacer sequence that is a polypeptide covalently bonded to the carrier-binding domain and the RecA or Rad51 polypeptide.

20. The system of claim 19 wherein the helix-loop-helix motif is derived from the LexA protein and the system comprises a RecA- LexA fusion polypeptide.

21. The system of claim 19 wherein the system comprises a RecA-Gal4 fusion protein.

22. The molecular tether of claim 12 wherein the carrier-binding domain comprises one or more zinc fingers.

* * * * *